(12) United States Patent
Sun

(10) Patent No.: US 8,394,823 B2
(45) Date of Patent: Mar. 12, 2013

(54) TRIAZOLOPYRIDINE COMPOUNDS USEFUL AS DGAT1 INHIBITORS

(75) Inventor: Chongqing Sun, East Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 340 days.

(21) Appl. No.: 12/936,997

(22) PCT Filed: Apr. 10, 2009

(86) PCT No.: PCT/US2009/040163
§ 371 (c)(1),
(2), (4) Date: Oct. 8, 2010

(87) PCT Pub. No.: WO2009/126861
PCT Pub. Date: Oct. 15, 2009

(65) Prior Publication Data
US 2011/0034506 A1    Feb. 10, 2011

Related U.S. Application Data

(60) Provisional application No. 61/044,142, filed on Apr. 11, 2008.

(51) Int. Cl.
A61K 31/437  (2006.01)
C07D 471/04  (2006.01)
A61P 3/04    (2006.01)
A61P 3/10    (2006.01)

(52) U.S. Cl. ................................ 514/303; 546/119
(58) Field of Classification Search .............. 514/303; 546/119
See application file for complete search history.

(56) References Cited

U.S. PATENT DOCUMENTS

| | | | |
|---|---|---|---|
| 6,043,369 A * | 3/2000 | Schefczik | 546/119 |
| 7,091,228 B2 | 8/2006 | Smith et al. | |
| 7,179,802 B2 | 2/2007 | Olson et al. | |
| 7,300,932 B2 | 11/2007 | Fox et al. | |
| 2006/0281750 A1 | 12/2006 | Li et al. | |
| 2006/0287324 A1 | 12/2006 | Sun et al. | |
| 2008/0064717 A1 | 3/2008 | Iyengar et al. | |

FOREIGN PATENT DOCUMENTS

| | | |
|---|---|---|
| EP | 0 404 190 | 10/1995 |
| EP | 1 785 424 | 5/2007 |
| WO | WO 98/08847 | 3/1998 |
| WO | WO 01/83481 | 11/2001 |
| WO | WO 02/12236 | 2/2002 |
| WO | WO 2004/017950 | 3/2004 |
| WO | WO 2004/026859 | 4/2004 |
| WO | WO 2004/047755 | 6/2004 |
| WO | WO 2004/107863 | 12/2004 |
| WO | WO 2005/072740 | 8/2005 |
| WO | WO 2005/077953 | 8/2005 |
| WO | WO 2006/018727 | 2/2006 |
| WO | WO 2006/019020 | 2/2006 |
| WO | WO 2007/113226 | 10/2007 |
| WO | WO 2007/138472 | 12/2007 |
| WO | WO 2008/006540 | 1/2008 |

OTHER PUBLICATIONS

U.S. Appl. No. 12/936,969, filed Oct. 8, 2010, Huang et al.
Arampatzis, S. et al., "Comparative enzymology of 11β-hydroxysteroid dehydrogenase type 1 from six species", Journal of Molecular Endocrinology, vol. 35, pp. 89-101 (2005).
El-Mobayed, M. et al., "Reactions with 6-Acetyl-3,5-diarylcyclohexen-1-ones and 2-Hydroxy-4,6-diaryl nicotinonitrile Synthesized by Michael Reactions from 3-Nitrobenzal-p-isopropyl Acetophenones and Some Studies with the Products", Egypt. J. Pharm. Sci., vol. 30, No. 1-4, pp. 329-337 (1989).

* cited by examiner

*Primary Examiner* — Niloofar Rahmani
(74) *Attorney, Agent, or Firm* — Burton Rodney

(57) ABSTRACT

Disclosed are triazolopyridine compounds of the following Formula (I); or stereoisomers or salts thereof. Also, disclosed are methods of using the compound in the treatment of obesity, dyslipidemia, diabetes and atherosclerosis, and to pharmaceutical compositions comprising at least one compound of Formula (I) or a stereoisomer or pharmaceutically acceptable salt thereof.

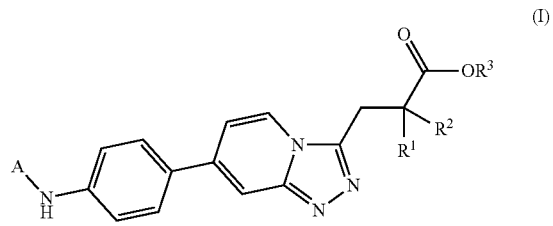

(I)

7 Claims, No Drawings

TRIAZOLOPYRIDINE COMPOUNDS USEFUL AS DGAT1 INHIBITORS

BACKGROUND

In mammals, diacylglycerol acyltransferase (DGAT) converts diacylglycerol to triacylglycerol in the final step of the triacylglycerol synthesis pathway. Decreasing triacylglycerol synthesis by inhibiting DGAT1 enzyme activity, therefore, is a strategy to treat obesity and obesity-related complications, dyslipidemia, diabetes, and atherosclerosis.

There are two biochemical pathways for the synthesis of triacylglycerol: the monoacylglycerol pathway, which occurs exclusively in the small intestine (Lehner, R. et al., *Prog. Lipid Res.*, 35:169-201 (1996)), and the glycerol-3-phosphate pathway, which takes place ubiquitously but most notably in the liver and in adipose tissue (Bell, R. M. et al., *Annu. Rev. Biochem.*, 49:459-487 (1980)). The monoacylglycerol pathway initiates from acyl coenzyme A:monoacylglycerol acyltransferase (MOAT) (EC 2.3.1.22). Within minutes of its appearance from the digestion of dietary fat in the lumen of the small intestine, 2-monoacylglycerol is acylated by MGAT to form diacylglycerol. Diacylglycerol is further acylated by acyl coenzyme A:diacylglycerol acyltransferase (DGAT) (EC 2.3.1.20) to re-synthesize triacylglycerol, which is packaged into chylomicron lipoprotein particles that eventually are secreted into the lymph. In the glycerol-3-phosphate pathway, two fatty acyl coenzyme A molecules are added to glycerol-3-phosphate to form phosphatidate. These reactions are followed by the removal of the phosphate group by phosphatidate phosphohydrolase to generate diacylglycerol. Diacylglycerol is then further acylated by DGAT to form triacylglycerol. Collectively, DGAT lies at the final step of both triacylglycerol synthesis pathways.

Two DGAT enzymes have been identified and have been designated as DGAT1 and DGAT2 (Cases, S. et al., *Proc. Natl. Acad. Sci. USA*, 95:13018-13023 (1998)) (Oelkers, P. et al., *J. Biol. Chem.*, 273:26765-26771 (1998)) (Cases, S. et al., *J. Biol. Chem.*, 276:38870-38876 (2001)). Although they carry out identical enzymatic reactions, DGAT1 and DGAT2 are encoded by two different genes that bear little sequence homology. Functionally, these two enzymes might have different physiological importance in vivo. DGAT1 knockout mice exhibit resistance towards becoming obese when challenged with a high fat (Smith, S. J. et al., *Nat. Genet.*, 25:87-90 (2000)). They are physically more active, possess a higher metabolic rate (Chen, H. C. et al., *Trends Cardiovasc. Med.*, 10:188-192 (2000)) and appear to have greater insulin sensitivity (Chen, H. C. et al., *J. Clin. Invest*, 109:1049-1055 (2002)). In contrast, DGAT2 knockout mice exhibit phenotypes such as lipopenia and skin barrier abnormalities, resulting in death soon after birth (Stone, S. J. et al., *J. Biol. Chem.*, 279:11767-11776 (2004)).

U.S. Pat. No. 7,300,932 B2 discloses fused bicyclic nitrogen-containing heterocyclic compounds that are useful for treating or preventing conditions and disorders associated with DGAT. As may be appreciated, there still remains a need for new compounds that are inhibitors of DGAT and are useful for the treatment of DGAT related conditions and disorders.

Applicants have found triazolopyridine compounds that have activity as inhibitors of DGAT, in particular DGAT1, and are thereby useful in therapy.

SUMMARY OF THE INVENTION

The present invention is directed to compounds having the following Formula (I):

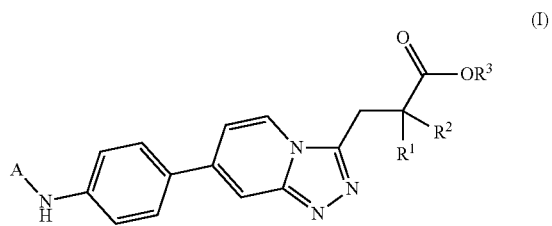

or stereoisomers or salts thereof, wherein:

A is alkyl, cycloalkyl, heterocyclyl, aryl, —C(O)R$^4$, —C(O)OR$^4$, or —C(O)NR$^4$R$^5$;

R$^1$ and R$^2$ are independently hydrogen, alkyl, —(CH$_2$)$_n$-(cycloalkyl), —(CH$_2$)$_n$-(aryl), —(CH$_2$)$_m$-(heterocyclyl), aryl, and/or heterocyclyl, or R$^1$ and R$^2$ together with the carbon atom to which they are attached, form a 3- to 7-membered cycloalkyl or 4- to 7-membered heterocyclyl ring with one or two heteroatoms;

n is an integer in the range of zero to 4;

R$^3$ is hydrogen or alkyl;

R$^4$ is alkyl, cycloalkyl, heterocyclyl, or aryl; and

R$^5$ is hydrogen or alkyl, or R$^4$ and R$^5$ together with the nitrogen atom to which they are attached, form a 4- to 7-membered heterocyclyl ring with one or two heteroatoms;

wherein:
each of said alkyl is substituted with 0-3 R$^a$;
each of said cycloalkyl is substituted with 0-3 R$^a$;
each of said heterocyclyl is substituted with 0-4 R$^b$; and
each of said aryl is substituted with 0-4 R$^b$;

R$^a$ is, independently at each occurrence, F, Cl, Br, —CF$_3$, —OH, —CN, —NR$^c$R$^d$, and/or C$_1$-C$_3$alkoxy;

R$^b$ is, independently at each occurrence, C$_1$-C$_4$alkyl, F, Cl, Br, —CF$_3$, —OH, —CN, —NR$^c$R$^d$, and/or C$_1$-C$_3$alkoxy; and R$^c$ and R$^d$ are, independently at each occurrence, H and/or C$_1$-C$_4$alkyl, or R$^c$ and R$^d$ together with the nitrogen atom to which they are attached, form a 4- to 7-membered heterocyclyl ring with one or two heteroatoms.

Also described is a pharmaceutical composition comprising a compound of Formula (I) or a stereoisomer or salt thereof; and a pharmaceutically acceptable carrier or diluent.

Further described is a method for treating a condition or disorder comprising administering to a patient in need thereof at least one compound of Formula (I) or a stereoisomer or pharmaceutically acceptable salt thereof; wherein said condition or disorder is obesity, dyslipidemia, diabetes, or atherosclerosis.

DETAILED DESCRIPTION

Listed below are definitions of various terms used to describe the present invention. These definitions apply to the terms as they are used throughout the specification (unless they are otherwise limited in specific instances) either individually or as part of a larger group.

The term "alkyl" and "alk" refer to a straight or branched chain alkane (hydrocarbon) radical containing from 1 to 12 carbon atoms, preferably from 1 to 6 carbon atoms, and more preferably from 1 to 4 carbon atoms. Exemplary "alkyl" and/or "alk" groups include, but are not limited to, for example, methyl, ethyl, propyl, butyl, pentyl, hexyl, isohexyl, heptyl, octyl, nonyl, decyl, and dodecyl.

The term "lower alkyl" refers to an "alkyl" and/or "alk" group containing from 1 to 4 carbon atoms and preferably from 1 to 2 carbon atoms. When a subscript is used with reference to an alkyl or other group, the subscript refers to the number of carbon atoms the group may contain. For example, the term "$C_0$-$C_4$alkyl" includes a bond and an alkyl group containing 1 to 4 carbon atoms, and the term "$C_1$-$C_4$alkyl" refers to alkyl groups containing 1 to 4 carbon atoms. Exemplary lower alkyl groups include, but are not limited to, for example, methyl, ethyl, propyl including n-propyl and isopropyl, and butyl including n-butyl, isobutyl, and t-butyl.

The "alkyl" and/or "alk" group can be optionally substituted with one or more substituents, preferably 1 to 3 substituents, at any available and substitutable position. Exemplary substituents include halogen (e.g., a single halo substituent or multiple halo substituents form, in the latter case, groups such as, for example, a perfluoroalkyl group or an alkyl group bearing —$CCl_3$ or —$CF_3$), hydroxyl, —$NH_2$, —NH(alkyl), —N(alkyl)$_2$, cyano, and $C_1$-$C_3$alkoxy group.

The term "cycloalkyl" refers to a fully saturated hydrocarbon group containing from 1 to 4 rings and 3 to 8 carbon atoms per ring. Exemplary cycloalkyl groups include, but at not limited to, for example, cyclopropyl, cyclobutyl, cyclopentyl, cyclohexyl, and cycloheptyl. The cycloalkyl group can be optionally substituted with one or more substituents, preferably 1 to 3 substituents, at any available and substitutable point of attachment. Exemplary substituents include those groups recited for substituted alkyl.

The term "aryl" refers to cyclic aromatic hydrocarbon groups having from 1 to 2 aromatic rings, such as, for example, phenyl, biphenyl, or naphthyl. When the aryl group contains two aromatic rings (e.g., bicyclic, etc.) the aromatic rings may be joined at a single point (e.g., biphenyl) or fused (e.g., naphthyl and phenanthrenyl). The aryl group can be optionally substituted with one or more substituents, preferably 1 to 4 substituents, at any available and substitutable ring position, or where valence allows on any rings fused or attached thereto. Exemplary substituents include alkyl and those groups recited for substituted alkyl.

The term "heterocyclo", "heterocycle", "heterocyclyl" or "heterocyclic ring", as used herein, represents an unsubstituted or substituted stable 4- to 7-membered monocyclic ring system which may be saturated, partially saturated, or fully unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. The heterocycle, heterocyclic, or heterocyclo group can be substituted at any available point of attachment with at least one substituent, preferably 1 to 4 substituents, selected from alkyl and those recited for substituted alkyl. When the term "heterocycle" is used, it is intended to include heteroaryl. The heterocyclo, heterocycle, heterocyclic, or heterocyclo group can be substituted at any available point of attachment with at least one substituent, preferably 1 to 4 substituents, selected from alkyl and those recited for substituted alkyl.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, carbolinyl, chromenyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl.

As used herein, the term "aromatic heterocyclic group" or "heteroaryl" is intended to mean fully unsaturated heterocyclyl rings, including monocyclic and polycyclic aromatic hydrocarbons having at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl indazolyl, indolinyl, 1,2,4-thiadiazolyl, isothiazolyl, purinyl, carbazolyl, benzimidazolyl, benzodioxolanyl, and benzodioxane. Heteroaryl groups are unsubstituted or substituted. Heteroaryl groups can be substituted at any available point of attachment with at least one substituent, preferably 1 to 4 substituents, selected from alkyl and those recited for substituted alkyl.

The term "alkoxy" as employed herein alone or as part of another group includes an alkyl as defined above linked through an oxygen atom.

The term "halogen" or "halo" as used herein alone or as part of another group refers to fluorine, chlorine, bromine, and iodine, with fluorine, chlorine, and bromine being preferred.

The term "cyano," as used herein, refers to a —CN group.

The term "methylene," as used herein, refers to a —CH$_2$— group.

The compounds of Formula (I) can be present as salts, which are also within the scope of this invention. Pharmaceutically acceptable (i.e., non-toxic, physiologically acceptable) salts are preferred. If the compounds of Formula (I) have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C$_1$-C$_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of Formula (I) having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di-, or tri-lower alkylamine, for example ethyl, text-butyl, diethyl, diisopropyl, triethyl, tributyl or dimethylpropylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula (I) or their pharmaceutically acceptable salts, are also included.

Preferred salts of the compounds of Formula (I) which contain a basic group include monohydrochloride, hydrogensulfate, methanesulfonate, phosphate, nitrate or acetate.

Preferred salts of the compounds of Formula (I) which contain an acid group include sodium, potassium and magnesium salts and pharmaceutically acceptable organic amines.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "bioactive metabolite" as employed herein refers to any functional group contained in a compound of Formula (I) with an open valence for further substitution wherein such substitution can, upon biotransformation, generate a compound of Formula (I). Examples of such functional groups of bioactive metabolites include, but are not limited to, —OH, —NH$_2$, or functional groups wherein the hydrogen can be replaced with a functional group such as —PO$_3$H$_2$ for example, which, upon biotransformation generates an —OH or —NH$_2$ functional group of a compound of Formula (I).

The term "prodrug" as employed herein includes functionalization of bioactive amine- or hydroxyl-containing compounds of Formula (I) to form alkyl-, acyl-, sulfonyl-, phosphoryl-, or carbohydrate-substituted derivatives. Such derivatives are formed by reacting compounds of Formula (I) with alkylating-, acylating-, sulfonylating-, or phosphorylating reagents employing procedures known to those skilled in the art. Alkylation of amines of Formula (I) may result in, but is not limited to, derivatives that include spacer units to other prodrug moieties such as substituted alkyoxymethyl-, acyloxymethyl-, phosphoryloxymethyl-, or sulfonyloxymethyl-groups. Alkylation of amines of Formula (I) may result in the generation of quarternary amine salts that act in vivo to provide the bioactive agent (i.e., the compound of Formula (I)).

Preferred prodrugs consist of a compound of Formula (I) where a pendant hydroxyl is phosphorylated to generate a phosphate derivative. Such a prodrug may also include a spacer group between the compound of Formula (I) and the phosphate group, such as a methyleneoxy-group. Methods to generate such a prodrug from a compound of Formula (I) are known to those skilled in the art, and are listed in the references below.

Preferred prodrugs also consist of a compound of Formula (I) where a pendant amine, such as a pyridine group, is alkylated with a group, such as methyl, to form a quarternary ammonium ion salt. Methods to generate such a prodrug from a compound of Formula (I) are known to those skilled in the art, and are listed in the references below.

Any compound that can be converted in vivo to provide the bioactive agent (i.e., the compound of Formula (I)) is a prodrug within the scope and spirit of the invention.

Various forms of prodrugs are well known in the art. A comprehensive description of prodrugs and prodrug derivatives are described in:

a) *The Practice of Medicinal Chemistry*, Camille G. Wermuth et al., Ch. 31 (Academic Press, 1996);

b) *Design of Prodrugs*, edited by H. Bundgaard (Elsevier, 1985);

c) *A Textbook of Drug Design and Development*, P. Krogsgaard-Larson and H. Bundgaard, eds., Ch. 5, pp. 113-191 (Harwood Academic Publishers, 1991);

d) *Hydrolysis in Drug and Prodrug Metabolism*, B. Testa and J. M. Mayer (Verlag Helvetica Chimica Acta AG, Zurich, Switzerland; Wiley-VCH, Weinheim, Federal Republic of Germany, 2003);

e) Ettmayer, P. et al., "Lessons Learned from Marketed and Investigational Prodrugs", *J. Med. Chem.*, 47(10):2393-2404 (2004); and f) Davidsen, S. K. et al., "N-(Acyloxyalkyl)pyridinium Salts as Soluble Prodrugs of a Potent Platelet Activating Factor Antagonist", *J. Med. Chem.*, 37 (26), 4423-4429 (1994).

The term "patient" as used herein encompasses all mammalian species including humans, cows, horses, dogs, and cats; and preferably, humans.

The term "therapeutically effective" is intended to qualify the amount of each agent, which will treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration.

All isotopes and stereoisomers of the compounds of the instant invention are contemplated, either in mixture or in pure or substantially pure form. The compounds of the present invention can have asymmetric centers at any of the carbon atoms including any one of the R substituents. Consequently, compounds of Formula (I) can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic techniques, chiral HPLC or fractional crystallization.

In one embodiment, a compound of Formula (I) or stereoisomers or salts thereof are provided wherein: A is $C_1$-$C_6$alkyl, $C_3$-$C_7$cycloalkyl, 1- or 2-ring heterocyclyl, 1- or 2-ring aryl, —C(O)$R^4$, —C(O)O$R^4$, or —C(O)N$R^4R^5$; $R^1$ and $R^2$ are independently hydrogen, $C_1$-$C_6$alkyl, —(CH$_2$)$_n$—($C_3$-$C_7$cycloalkyl), aryl, and/or 1- or 2-ring heterocyclyl, or $R^1$ and $R^2$ together with the carbon atom to which they are attached, form a 3- to 7-membered cycloalkyl or 4- to 7-membered heterocyclyl ring with one or two heteroatoms; n is an integer in the range of zero to 2; $R^3$ is hydrogen or $C_1$-$C_6$alkyl; $R^4$ is $C_1$-$C_6$alkyl, $C_3$-$C_7$cycloalkyl, 1- or 2-ring heterocyclyl, or aryl; and $R^5$ is hydrogen or $C_1$-$C_6$alkyl, or $R^4$ and $R^5$ together with the nitrogen atom to which they are attached, form a 4- to 7-membered heterocyclyl ring with one or two heteroatoms; wherein: each of said alkyl is substituted with 0-3 $R^a$; each of said cycloalkyl is substituted with 0-3 $R^a$; each of said heterocyclyl is substituted with 0-4 $R^b$; and each of said aryl is substituted with 0-4 $R^b$; $R^a$ is, independently at each occurrence, F, Cl, Br, —CF$_3$, —OH, —CN, —N$R^cR^d$, and/or $C_1$-$C_3$alkoxy; $R^b$ is, independently at each occurrence, $C_1$-$C_4$alkyl, F, Cl, Br, —CF$_3$, —OH, —CN, —N$R^cR^d$, and/or $C_1$-$C_3$alkoxy; and $R^c$ and $R^d$ are, independently at each occurrence, H and/or $C_1$-$C_4$alkyl. Preferably, A is a 1- or 2-ring heterocyclyl or —C(O)N$R^4R^5$; and more preferably, A is a 1- or 2-ring heteroaryl.

In one embodiment, a compound of Formula (I) or stereoisomers or salts thereof are provided wherein: A is 1- or 2-ring heterocyclyl, or 1- or 2-ring aryl, $R^1$ and $R^2$ are independently hydrogen, $C_1$-$C_6$alkyl, —(CH$_2$)$_n$—($C_3$-$C_7$cycloalkyl), and/or aryl; wherein: each of said alkyl is substituted with 0-3 $R^a$; each of said cycloalkyl is substituted with 0-3 $R^a$; each of said heterocyclyl is substituted with 0-4 $R^b$; and each of said aryl is substituted with 0-4 $R^b$; $R^a$ is, independently at each occurrence, F, Cl, Br, —CF$_3$, —OH, —CN, —N$R^cR^d$, and/or $C_1$-$C_3$alkoxy; $R^b$ is, independently at each occurrence, $C_1$-$C_4$alkyl, F, Cl, Br, —CF$_3$, —OH, —CN, —N$R^cR^d$, and/or $C_1$-$C_3$alkoxy; and $R^c$ and $R^d$ are, independently at each occurrence, H and/or $C_1$-$C_4$alkyl. Preferably A is a 1- or 2-ring heteroaryl. Preferably $R^1$ is hydrogen, $C_1$-$C_4$alkyl or —(CH$_2$)$_n$—($C_5$-$C_7$-cycloalkyl). Preferably, n is 0 or 1. Preferably, $R^2$ is hydrogen or $C_1$-$C_4$alkyl. Preferably, $R^3$ is hydrogen or $C_1$-$C_4$alkyl.

In one embodiment, a compound of Formula (I) or stereoisomers or salts thereof are provided wherein: A is a 1- or 2-ring heterocyclyl having at least one heteroatom selected from S and N; $R^1$ is hydrogen, $C_1$-$C_4$alkyl or —(CH$_2$)$_n$—($C_3$-$C_7$-cycloalkyl); n is 0 or 1; $R^2$ is hydrogen or $C_1$-$C_4$alkyl; $R^3$ is hydrogen or $C_1$-$C_4$alkyl; and wherein said heterocyclyl is substituted with 0-2 $R^b$; and $R^b$ is, independently at each occurrence, F, Cl, Br, and/or —CF$_3$. Examples of suitable 1- and 2-ring heterocyclyls includes 1- and 2-ring heteroaryls such as benzothiazolyl.

In one embodiment, a compound of Formula (I) or stereoisomers or salts thereof are provided wherein: $R^1$ is hydrogen, propyl, butyl, cyclohexyl, or —CH$_2$-cyclohexyl; $R^2$ is hydrogen; $R^3$ is hydrogen or methyl; and A is

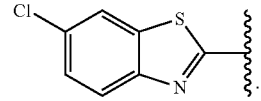

In one embodiment, a compound of Formula (I) or stereoisomers or salts thereof are provided wherein A is a heterocyclyl group. Preferably, A is an unsaturated heterocyclyl group, and more preferably, A is heteroaryl. Examples of suitable heteroaryl groups include 1- and 2-ring heteroaryl groups such as benzothiazolyl or chlorobenzothiazolyl.

In one embodiment, a compound of Formula (I) or stereoisomers or salts thereof are provided wherein $R^1$ and $R^2$ are independently hydrogen, alkyl, or —(CH$_2$)$_n$-(cycloalkyl); and n is an integer in the range of zero to 4. When $R^1$ or $R^2$ is —(CH$_2$)$_n$-(cycloalkyl) and n is zero, then $R^1$ or $R^2$ is a cycloalkyl group. Preferably, $R^1$ and $R^2$ are hydrogen, $C_1$-$C_6$alkyl, or —(CH$_2$)$_n$—($C_3$-$C_6$cycloalkyl) wherein n is zero, 1, or 2. More preferably, $R^1$ is hydrogen, $C_1$-$C_4$alkyl, or —(CH$_2$)$_n$—($C_3$-$C_6$cycloalkyl) wherein n is zero or 1; and $R^2$ is hydrogen or $C_1$-$C_4$alkyl. Still more preferably, $R^1$ is hydrogen, $C_1$-$C_4$alkyl, cyclohexyl, or —(CH$_2$)-(cyclohexyl); and $R^2$ is hydrogen.

In one embodiment, a compound of Formula (I) or stereoisomers or salts thereof are provided wherein $R^3$ is hydrogen or $C_1$-$C_6$alkyl. Preferably, $R^3$ is hydrogen or $C_1$-$C_4$alkyl; and more preferably, $R^3$ is hydrogen, methyl, or ethyl. Still more preferably, $R^3$ is hydrogen or methyl.

In one embodiment, a compound of Formula (I) or a salt thereof is provided, wherein said compound is:
(S)-2-((7-(4-(6-chlorobenzo[d]thiazol-2-ylamino)phenyl)-[1,2,4]triazolo[4,3-a]pyridin-3-yl)methyl)-3-methylbutanoic acid (1);
(S)-methyl 2-((7-(4-(6-chlorobenzo[d]thiazol-2-ylamino)phenyl)-[1,2,4]triazolo[4,3-a]pyridin-3-yl)methyl)-3-methylbutanoate (1F);
(R)-2-((7-(4-(6-chlorobenzo[d]thiazol-2-ylamino)phenyl)-[1,2,4]triazolo[4,3-a]pyridin-3-yl)methyl)-3-methylbutanoic acid (2);
(R)-methyl 2-((7-(4-(6-chlorobenzo[d]thiazol-2-ylamino)phenyl)-[1,2,4]triazolo[4,3-a]pyridin-3-yl)methyl)-3-methylbutanoate (2B);
(R)-2-((7-(4-(6-chlorobenzo[d]thiazol-2-ylamino)phenyl)-[1,2,4]triazolo[4,3-a]pyridin-3-yl)methyl)-4-methylpentanoic acid (3);
(R)-methyl 2-((7-(4-(6-chlorobenzo[d]thiazol-2-ylamino)phenyl)-[1,2,4]triazolo[4,3-a]pyridin-3-yl)methyl)-4-methylpentanoate (3B);
(S)-2-((7-(4-(6-chlorobenzo[d]thiazol-2-ylamino)phenyl)-[1,2,4]triazolo[4,3-a]pyridin-3-yl)methyl)-4-methylpentanoic acid (4);
(S)-methyl 2-((7-(4-(6-chlorobenzo[d]thiazol-2-ylamino)phenyl)-[1,2,4]triazolo[4,3-a]pyridin-3-yl)methyl)-4-methylpentanoate (4B);
(R)-2-((7-(4-(6-chlorobenzo[d]thiazol-2-ylamino)phenyl)-[1,2,4]triazolo[4,3-a]pyridin-3-yl)methyl)hexanoic acid (5);
(R)-3-(7-(4-(6-chlorobenzo[d]thiazol-2-ylamino)phenyl)-[1,2,4]triazolo[4,3-a]pyridin-3-yl)-2-(cyclohexylmethyl)propanoic acid (6);

(S)-3-(7-(4-(6-chlorobenzo[d]thiazol-2-ylamino)phenyl)-[1,2,4]triazolo[4,3-a]pyridin-3-yl)-2-cyclohexylpropanoic acid (7); or 3-(7-(4-(6-chlorobenzo[d]thiazol-2-ylamino)phenyl)-[1,2,4]triazolo[4,3-a]pyridin-3-yl)propanoic acid (8).

The compounds of Formula (I) are useful as DGAT modulators, and include compounds which are, for example, activators or inhibitors of DGAT enzyme. Accordingly, the compounds of Formula (I) may be useful for the treatment or prevention of diseases and disorders associated with DGAT enzyme activities. Preferably, compounds of Formula (I) possess activity as inhibitors of DGAT enzyme activities, and may be used in the treatment of diseases or disorders associated with the activity of the DGAT enzyme.

The compounds of Formula (I) or stereoisomers or therapeutically acceptable salts thereof can be administered to mammals, preferably humans, for the treatment of a variety of conditions and disorders, including, but not limited to metabolic as well as conditions associated with metabolic disorders, (e.g., obesity, diabetes, arteriosclerosis, hypertension, polycystic ovary disease, cardiovascular disease, osteoarthritis, dermatological disorders, hypertension, insulin resistance, hypercholesterolemia, hypertriglyceridemia, cholelithiasis and sleep disorders, hyperlipidemic conditions, bulimia nervosa and compulsive eating disorders). These compounds could also be used for treatment of catabolism in connection with pulmonary dysfunction and ventilator dependency; treatment of cardiac dysfunction (e.g., associated with valvular disease, myocardial infarction, cardiac hypertrophy or congestive heart failure); and improvement of the overall pulmonary function; transplant rejection; rheumatoid arthritis; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury.

The compounds of Formula (I) can possess both DGAT and ACAT inhibitory activities. ACAT inhibition is a known mechanism to provide hypolipidemic effects (which also has anti-atherosclerosis activity) such as disclosed in, *Drugs of the Future*, 24:9-15 (1999) (Avasimibe); Nicolosi et al., "The ACAT inhibitor, C1-1011 is effective in the prevention and regression of aortic fatty streak area in hamsters", *Atherosclerosis* (Shannon, Irel.), 137(1):77-85 (1998); Ghiselli, G., "The pharmacological profile of FCE 27677: a novel ACAT inhibitor with potent hypolipidemic activity mediated by selective suppression of the hepatic secretion of ApoB100-containing lipoprotein", *Cardiovasc. Drug Rev.*, 16(1):16-30 (1998); Smith, C. et al., "RP 73163: a bioavailable alkylsulfinyl-diphenylimidazole ACAT inhibitor", *Bioorg. Med. Chem. Lett.*, 6(1):47-50 (1996); Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways*, CRC Press, Inc., publ., Ruffolo, Jr., R. R. et al., eds., pp. 173-198 (1995); Sliskovic et al., "ACAT inhibitors: potential anti-atherosclerotic agents", *Curr. Med. Chem.*, 1(3):204-225 (1994); Stout et al., "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", *Chemtracts: Org. Chem.*, 8(6):359-362 (1995), or TS-962 (Taisho Pharmaceutical Co. Ltd.), as well as F-1394, CS-505, F-12511, HL-004, K-10085 and YIC-C8-434.

The present invention relates to the use of a DGAT inhibitor in the treatment of appetitive or motivational disorders that regulate desires to consume sugars, carbohydrates, alcohol or drugs and more generally to regulate the consumption of ingredients with hedonic value. In the present description and in the claims, appetitive disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present invention further relates to the use of a DGAT inhibitor for the treatment of bulimia and obesity, including obesity associated with type II diabetes (non-insulin-dependent diabetes), or more generally any disease resulting in the patient becoming overweight. Obesity, as described herein, is defined by a body mass index (kg/m$^2$) of at least 26. It may be due to any cause, whether genetic or environmental, including overeating and bulimia, polycystic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

As modulators of the DGAT enzyme, the compounds of the present invention are further useful for the treatment and prevention of respiratory diseases and disorders. Respiratory diseases for which DGAT modulators are useful include, but are not limited to, chronic pulmonary obstructive disorder, emphysema, asthma, and bronchitis. In addition, DGAT modulators block the activation of lung epithelial cells by moieties such as allergic agents, inflammatory cytokines or smoke, thereby limiting release of mucin, cytokines, and chemokines, or selectively inhibiting lung epithelial cell activation.

DGAT is important in the regulation of TNF alpha of adipocytes. Compounds of the present invention are especially of value, for example, in treating obesity associated inflammatory diseases such as arthritis or inflammatory bowel disease. In particular, the present compounds are useful for treating autoimmune glomerulonephritis and other instances of glomerulonephritis induced by deposition of immune complexes in the kidney that trigger Fc gamma receptor responses leading to kidney damage.

In one embodiment, a method is provided for treatment of a condition or disorder comprising administering to a patient in need thereof at least one compound of Formula (I) or a stereoisomer or pharmaceutically acceptable salt thereof; wherein said condition or disorder is obesity, dyslipidemia, diabetes, or atherosclerosis. Preferred compounds useful in the method of the present embodiment include compounds of Formula (I) or stereoisomers or salts thereof wherein: A is a 1- or 2-ring heterocyclyl having at least one heteroatom selected from S and N; $R^1$ is hydrogen, $C_1$-$C_4$alkyl or —$(CH_2)_n$—($C_5$-$C_7$cycloalkyl); n is 0 or 1; $R^2$ is hydrogen or $C_1$-$C_4$alkyl; $R^3$ is hydrogen or $C_1$-$C_4$alkyl; and wherein said heterocyclyl is substituted with 0-2 $R^b$; and $R^b$ is, independently at each occurrence, F, Cl, Br, and/or —$CF_3$. Examples of suitable 1- and 2-ring heterocyclyls includes 1- and 2-ring heteroaryls such as benzothiazolyl. Preferably, the method of this embodiment is used to treat obesity. Preferably, the patient is a human. Preferably, a therapeutically effective amount of the compound of Formula (I) or stereoisomer or a pharmaceutically acceptable salt thereof is administered in the method of this embodiment.

In one embodiment, the use of a compound of Formula (I) or a stereoisomer or pharmaceutically acceptable salt thereof, in the manufacture of a medicament for the treatment of a condition or disorder is provided, wherein the condition or disorder is obesity, dyslipidemia, diabetes, or atherosclerosis. Preferably, the condition or disorder is obesity.

In one embodiment, the use of a compound of Formula (I) or a stereoisomer or pharmaceutically acceptable salt thereof, in the manufacture of a medicament for the treatment of a condition or disorder is provided, wherein the condition or disorder is treatable by modulation of the DGAT1 enzyme. The modulation can be activation or inhibition of the DGAT1 enzyme. Preferably, the condition or disorder is treatable by inhibition of the DGAT 1 enzyme. Conditions or disorder treatable by the DGAT1 enzyme include, but are not limited to, obesity, dyslipidemia, diabetes, or atherosclerosis. Preferably, the condition or disorder treated by inhibition of the DGAT1 enzyme is obesity.

In one embodiment, a method is provided for treating a condition or disorder in a patient wherein the condition or disorder is dependent upon DGAT1 inhibition, comprising administering to the patient a compound of Formula (I) or a stereoisomer or a pharmaceutically acceptable salt thereof. The method of this embodiment can be used to treat conditions or disorders including obesity, dyslipidemia, diabetes, or atherosclerosis. Preferably, the condition or disorder is obesity. A therapeutically effective amount of a compound of Formula (I) or a stereoisomer or a pharmaceutically acceptable salt thereof is administered in the method of this embodiment.

The present invention includes within its scope pharmaceutical compositions comprising, as an active ingredient, a therapeutically effective amount of at least one of the compounds of Formula (I) or a stereoisomer or pharmaceutically acceptable salt thereof, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; agents used to treat eating disorders, cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents. Such other therapeutic agent(s) may be administered prior to, simultaneously with, or following the administration of the DGAT inhibitors in accordance with the invention.

Examples of suitable anti-obesity agents for use in combination with the compounds of the present invention include melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonist, NPY2 and NPY4 modulators, amylin receptor modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491, 134, 5,776,983 and 5,488,064, a thyroid receptor beta modulator, such as a thyroid receptor ligand as disclosed in WO 97/21993 (U. Cal SF), WO 99/00353 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/AXOKINE® (Regeneron), BDNF (brain-derived neurotrophic factor), leptin and leptin receptor modulators, or cannabinoid-1 (CB1) receptor antagonists, such as SR-141716 (Sanofi), MK-0364 (Merck), CP-945,598 (Pfizer) or SLV-319 (Solvay).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DPP4) inhibitors, SGLT2 inhibitors, glucokinase inhibitors, AMP kinase modulators, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594, 016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present invention may be employed with a PPAR α/γ dual agonist such as MK-767/KRP-297 (Merck/Kyorin; as described in Yajima, K. et al., *Am. J. Physiol. Endocrinol. Metab.*, 284:E966-E971 (2003)), AZ-242 (tesaglitazar; Astra-Zeneca; as described in Ljung, B. et. al., *J. Lipid Res.*, 43:1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., *J. Med. Chem.*, 31:1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A. et al., *Current Pharmaceutical Design*, 2:1-40 (1996).

In addition, other squalene synthetase inhibitors suitable for use herein include the terpenoid pyrophosphates disclosed by Ortiz de Montellano, P. et al., *J. Med. Chem.*, 20:243-249 (1977), the farnesyl diphosphate analog A and presqualene pyrophosphate (PSQ-PP) analogs as disclosed by Corey et al., *J. Am. Chem. Soc.*, 98:1291-1293 (1976), phosphinylphosphonates reported by McClard, R. W. et al., *J. Am. Chem. Soc.*, 109:5544 (1987) and cyclopropanes reported by Capson, T. L., PhD dissertation, June, 1987, Dept. Med. Chem. U of Utah, Abstract, Table of Contents, pp. 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-SEPHADEX® (SECHOLEX®, policexide) and cholestagel (Sankyo/Geltex), as well as LIPOSTABIL® (Rhone-Poulenc), EISAI® E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis*, 115:45-63 (1995) and *J. Med. Chem.*, 41:973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal Na$^+$/bile acid cotransporter inhibitor such as disclosed in *Drugs of the Future*, 24:425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equal, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinal as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

DGAT inhibitors could be useful in treating other diseases associated with obesity, including sleep disorders. Therefore, the compounds described in the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

The compounds described in the present invention could be used in combination with suitable anti-inflammatory agents. Examples of suitable anti-inflammatory agents for use in combination with the compounds of the present invention include prednisone, dexamethasone, cyclooxygenase inhibitors (i.e., COX-1 and/or COX-2 inhibitors such as NSAIDs, aspirin, indomethacin, ibuprofen, piroxicam, naproxen, CELEBREX®, VIOXX®), CTLA4-Ig agonists/antagonists, CD40 ligand antagonists, IMPDH inhibitors, such as mycophenolate (CELLCEPT®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384, including TNF-alpha inhibitors, such as tenidap, anti-TNF antibodies or soluble TNF receptor such as etanercept (ENBREL®), rapamycin (sirolimus or RAPAMUNE®) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., ZELNORM® and Maxi-K openers such as those disclosed in U.S. Pat. No. 6,184,231 B1).

The above other therapeutic agents, when employed in combination with the compounds of the present invention, may be used, for example, in those amounts indicated in the Physicians' Desk Reference (PDR) or as otherwise determined by one of ordinary skill in the art.

Also embraced within this invention is a class of pharmaceutical compositions comprising the compound of Formula (I) or a stereoisomer or a pharmaceutically acceptable salt thereof in association with one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

The compounds of the present invention can be administered to various mammalian species known to be subject to such maladies, e.g., humans, in an effective amount up to 1 gram, preferably up to 200 mg, more preferably up to 100 mg in a regimen of single, two or four divided daily doses.

The compounds of the present invention can be administered for any of the uses described herein by any suitable means, for example, orally, such as in the form of tablets, capsules, granules or powders; sublingually; bucally; parenterally, such as by subcutaneous, intravenous, intramuscular, or infrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a fowl suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of Formula (I) can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

The compounds of the present invention can be prepared as shown in the following reaction schemes and description thereof, as well as relevant published literature procedures that may be used by one skilled in the art. Exemplary reagents and procedures for these reactions appear hereinafter and in the working Examples.

ABBREVIATIONS

The following abbreviations are employed in the Schemes, Examples and elsewhere herein:
DMF=N,N-dimethylformamide
DIPEA=diisopropylethylamine
DMSO=dimethyl sulfoxide
EDC=N-(3-dimthylaminopropyl)-N'-ethylcarbodiimide
EtOAc=ethyl acetate
EtOH=ethanol
Et$_3$N=triethylamine
HCl=hydrochloric acid
HOBt=1-hydroxybenzotriazole
HPLC or LC=high performance liquid chromatography
K$_2$CO$_3$=potassium carbonate
LiOH=lithium hydroxide
MeOH=methanol
MS or Mass Spec=mass spectrometry
NaCl=sodium chloride
NaHCO$_3$=sodium bicarbonate
Na$_2$CO$_3$=sodium carbonate
Na$_2$SO$_4$=sodium sulfate
Ph$_3$PCl$_2$=triphenylphosphine dichloride
PG=protecting group
Pd(dppf)Cl$_2$=[1,1'-bis(diphenylphosphino)-ferrocene] dichloropalladium(II)
Pd(Ph$_3$P)$_4$=tetrakis(triphenylphosphine)palladium(0)
TEA=trifluoroacetic acid
THF=tetrahydrofuran
min=minute(s)
h=hour(s)
L=liter
mL=milliliter
μL=microliter
g=gram(s)
mg=milligram(s)
mol=moles
mmol=millimole(s)
nM=nanomolar The compounds of the present invention can be prepared in a number of ways known to one skilled in the art of organic synthesis. The compounds of the present invention may be prepared by the methods described below, other with synthetic methods known in the art of synthetic organic chemistry, or by variations thereon as appreciated by those skilled in the art. The reactions are performed in a solvent or solvent mixture appropriate to the reagents and materials employed and suitable for the transformation being effected. It will be understood by those skilled in the art of organic synthesis that the functionality present on the molecule should be consistent with the transformation proposed. This will sometimes require a judgment to modify the order of the synthetic steps or to select one particular process scheme over another in order to obtain a desired compound of the invention.

The compounds of Formula (I) can be prepared according to the general method shown in the scheme below. Solvents, temperatures, pressures, and other reaction conditions may readily be selected by one of ordinary skill in the art. Starting materials are commercially available or can be readily prepared by one of ordinary skill in the art using known methods. For the scheme and compounds described below, A, R$^1$, R$^2$ and R$^3$ are as described for a compound of Formula (I).

The following are the definitions of symbols used throughout the scheme:

PG is a suitable nitrogen protecting group, exemplified by benzyl, tert-butoxycarbonyl-[BOC], benzyloxycarbonyl-[CBZ], or 9-fluorenylmethoxycarbonyl-[FMOC].

LG is a leaving group exemplified by halogen (Cl, Br, I) and sulfonates (—OSO$_2$-aryl —OSO$_2$Ph or —OSO$_2$PhCH$_3$), or —OSO$_2$-alkyl (e.g., —OSO$_2$CH$_3$ or —OSO$_2$CF$_3$)).

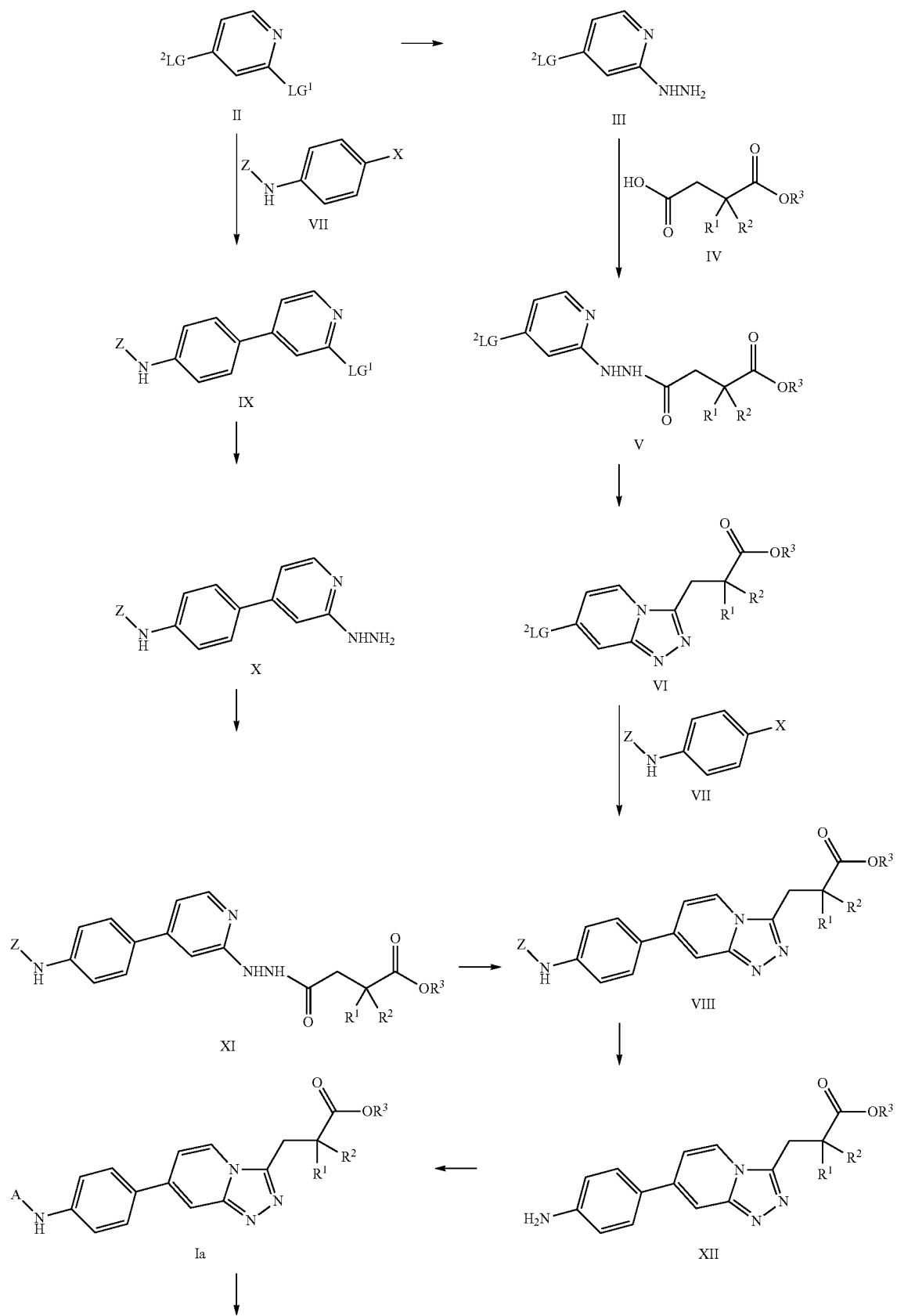
Scheme

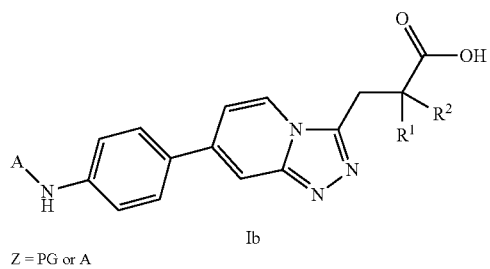

Ib

Z = PG or A

Compounds of formula II are either commercially available or available by means known to one skilled in the art. Compounds of formula III can be prepared by reacting compounds of formula II with anhydrous hydrazine in a polar solvent, such as 1,4-dioxane or pyridine at elevated temperature. Compounds of formula V can be prepared by reacting compounds of formula III with a compound of formula IV in the presence of a coupling agent, such as N-[3-(dimethylaminopropyl)-N'-ethylcarbodiimide. Compounds of formula IV are either commercially available or available by means known to one skilled in the art. Compounds of formula VI can be prepared by activation of a compound of formula V with a phosphonium salt, such as triethylphosphine in the presence of carbon tetrachloride or dichlorotriphenylphosphorane. Compounds of formula VIII can be prepared by cross coupling compounds of formula VI with an activated compound of formula VII where X is a boronic ester or a tin reagent in the presence of an appropriate catalyst, such as Pd(Ph$_3$P)$_4$. Compounds of formula VII (where Z is an N-protecting group (PG) or a functional group (A)) are either commercially available or available by means known to one skilled in the art.

Alternatively, compounds of formula VIII can be prepared by a modified route shown in the scheme. Compounds of formula IX can be prepared by cross coupling of compounds of formula II with a compound of formula VII where X is a boronic ester or a tin reagent in the presence of an appropriate catalyst, such as Pd(Ph$_3$P)$_4$. Compounds of formula X can be prepared by reacting compounds of formula IX with anhydrous hydrazine in a polar solvent, such as 1,4-dioxane or pyridine at elevated temperature. Compounds of formula XI can be prepared by reaction of compounds of formula X with a compound of formula IV in the presence of a coupling agent, such as N-[3-(dimethylaminopropyl)-N'-ethylcarbodiimide. Compounds of formula VIII can be prepared by activation of a compound of formula XI with a phosphonium salt, such as triethylphosphine in the presence of carbon tetrachloride or dichlorotriphenyl-phosphorane.

Compounds of formula XII can be prepared from compounds of formula VIII where Z is an N-protecting group by the methods described in Greene, T. W. et al., *Protecting Groups in Organic Synthesis*, John Wiley & Sons, Inc, New York (1991). Compounds of formula Ia where A is —C(O)R$^4$ can be prepared by acylation of compounds of formula XII with an acyl chloride or anhydride in the presence of a bas; such as triethylamine. Compounds of formula Ia where A is —C(O)R$^4$ can be prepared by reaction of compounds of formula XII with a chloroformate in the presence of a base, such as triethylamine. Compounds of formula Ia where A is —C(O)NR$^4$R$^5$ can be prepared by reaction of compounds of formula XII with an isocyanate in the presence of a base, such as triethylamine. Compounds of formula Ib can be prepared by saponification of compounds of formula Ia in aqueous THF in the presence of a base, such as lithium hydroxide, followed by acidification.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited to the illustrative examples set forth herein below, but rather defined by the claims appended thereto.

General

The following methods were used in the working examples, except where noted otherwise.

Analytical HPLC and HPLC/MS Methods Employed in Characterization of Examples

Reverse phase analytical HPLC was performed on Shimadzu LC10AS systems and reverse phase analytical HPLC/MS on Shimadzu LC10AS systems coupled with Waters ZMD Mass Spectrometers using the following methods:
Method A. Linear gradient of 10 to 100% solvent B over 2 min, with 1 min hold at 100% B;
UV visualization at 220 nm
Column: PHENOMENEX® Luna C18 4.6×30 mm
Flow rate: 1.0 ml/min
Solvent A: 0.1% trifluoroacetic acid, 10% water, 90 methanol.
Solvent B: 0.1% trifluoroacetic acid, 90% methanol, 10% water.
Method B. Linear gradient of 0 to 100% solvent B over 4 min, with 1 min hold at 100% B;
UV visualization at 220 nm
Column: PHENOMENEX® Luna C18 4.6×50 mm
Flow rate: 4 ml/min
Solvent A: 0.1% trifluoroacetic acid, 90% water, 10% methanol.
Solvent B: 0.1% trifluoroacetic acid, 90% methanol, 10% water.
Method C. Linear gradient of 0 to 100% solvent B over 4 min, with 1 min hold at 100% B;
UV visualization at 220 nm
Column: PHENOMENEX® Luna C18 4.6×50 mm
Flow rate: 4 ml/min Solvent A: 10 mM ammonium acetate, 90% water, 10% acetonitrile.
Solvent B: 10 mM ammonium acetate, 90% acetonitrile, 10% water.
Method D. Isocratic of 25% solvent A and 75% of solvent B over 25 min;
UV detection at 351 nm
Chiral column: Wheck-01 (R,R), 250×4.6 mm ID, 10 μm) at 27° C.
Flow rate: 1 ml/min
Solvent A: 0.1% trifluoroacetic acid in EtOH.
Solvent B: 0.1% trifluoroacetic acid in heptane.

NMR Employed in Characterization of Examples $^1$H NMR spectra were obtained with Bruker or JEOL Fourier transform spectrometers operating at frequencies as follows: $^1$H NMR: 400 MHz (Bruker or JEOL) or 500 MHz (JEOL). $^{13}$C NMR: 100 MHz (Bruker or JEOL). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for CD$_2$HSOCD$_3$, 3.30 ppm for CD$_2$HOD, and 7.24 ppm for CHCl$_3$, and which in $^{13}$C NMR spectra appear at 39.7 ppm for CD$_3$SOCD$_3$, 49.0 ppm for CD$_3$OD, and 77.0 ppm for CDCl$_3$. All $^{13}$C NMR spectra were proton decoupled.

Example 1

(S)-2-((7-(4-(6-Chlorobenzo[d]thiazol-2-ylamino)phenyl)-[1,2,4]triazolo[4,3-a]pyridin-3-yl)methyl)-3-methylbutanoic acid (1)

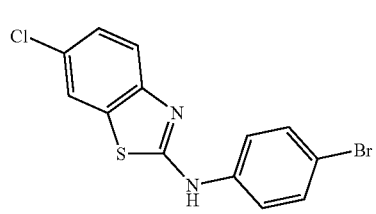

Preparation 1A:
N-(4-Bromophenyl)-6-chlorobenzo[d]thiazol-2-amine (1A)

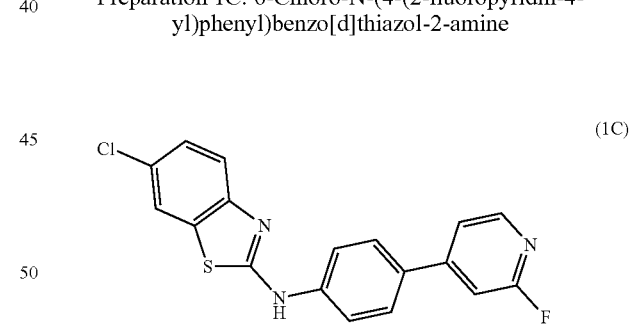

To a suspension of 2,6-dichlorobenzothiazole (2.52 g, 12.3 mmol) and 4-bromoaniline (2.12 g, 12.2 mmol) in EtOH (15 mL) was added 4 N HCl in dioxane (0.2 mL, 0.8 mmol). The reaction mixture was stirred at 140° C. in a microwave reactor for 1 h. After cooling to room temperature, the resulting suspension was filtered. The collected solid was washed with MeOH (10 mL), and dried in a 50° C. vacuum oven for 16 h to afford 3.28 g (80%) of the title compound as a white solid. HPLC/MS (method C): retention time=4.24 min, [M+H]$^+$= 339.0.

Preparation 1B: 6-Chloro-N-(4-(4,4,5,5-tetramethyl-1,3,2-dioxaborolan-2-yl)phenyl)benzo[d]thiazol-2-amine (1B)

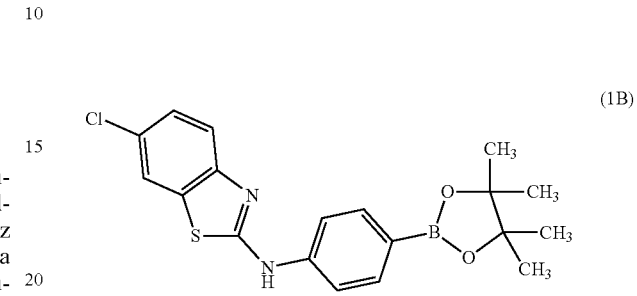

A mixture of Compound 1A (32 g, 9.5 mmol), 4,4,4',4',5,5,5',5'-octamethyl-2,2'-bi(1,3,2-dioxaborolane) (2.52 g, 9.94 mmol), potassium acetate (2.78 g, 28.4 mmol) and Pd(dppf)Cl$_2$ (387 mg, 0.47 mmol) in dioxane (50 mL) was stirred at 85° C. under argon for 2 h. Analysis by LC/MS indicated about 50% starting material was consumed. An additional amount of Pd(dppf)Cl$_2$ (100 mg, 0.12 mmol) was added. The reaction mixture continued stirring at 85° C. under argon for 16 h. After cooling to room temperature, the reaction mixture was diluted with water, extracted with EtOAc (150 mL×2). The organic extracts were washed with brine, dried over Na$_2$SO$_4$, filtered and concentrated. The obtained crude residue was purified using a silica gel cartridge (120 g) eluting with a gradient of EtOAc (0-30%) in hexanes to give 1.82 g (52%) of the title compound as a white solid. HPLC/MS (method B): retention time=4.32 min, [M+H]$^+$=387.2.

Preparation 1C: 6-Chloro-N-(4-(2-fluoropyridin-4-yl)phenyl)benzo[d]thiazol-2-amine (1C)

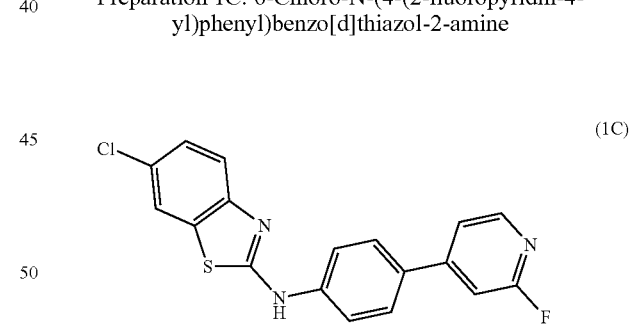

To a suspension of Compound 1B (233 mg, 0.63 mmol), 2-fluoro-4-bromopyridine (100 mg, 0.57 mmol), potassium carbonate (175 mg, 1.26 mmol) in dioxane (3 mL) and water (1 mL) was added Pd(Ph$_3$P)$_4$ (60 mg, 0.057 mmol). The resulting yellow suspension was stirred at 100° C. for 3 h. After cooling to room temperature, the reaction mixture containing white precipitates was diluted with EtOAc (50 mL). The resulting cloudy EtOAc solution was washed with water (2×20 mL), concentrated under reduced pressure to give an off-white solid, which was triturated with EtOAc (5 mL). The resulting suspension was filtered, and the collected solid rinsed with small amount of EtOAc to give a white solid. The filtrate was then concentrated under reduced pressure and the obtained solid residue triturated with EtOAc, and this process was repeated three times. Altogether, 90 mg (44%) of the title compound as a white solid was obtained. HPLC/MS (method B): retention time=4.15 min, [M+H]⁺=355.9.

Preparation 1D: 6-Chloro-N-(4-(2-hydrazinylpyridin-4-yl)phenyl)benzo[d]thiazol-2-amine

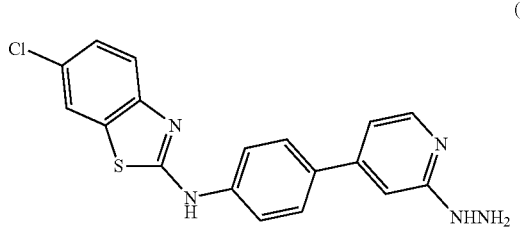

(1D)

To a solution of Compound 1C (85 mg, 0.24 mmol) in pyridine (0.5 mL) was added 0.1 mL of anhydrous hydrazine. The resulting mixture was stirred at 75° C. for 3 h. Analysis by LC/MS indicated that the majority of the starting Compound 1C remained. An additional amount of anhydrous hydrazine (0.1 mL) was added and the reaction continued at 75° C. for 17 h. After cooling to room temperature, the reaction mixture was concentrated under reduced pressure to dryness. To the obtained residue was added water (5 mL) and the resulting suspension was filtered. The collected yellowish solid was rinsed with water (20 mL), dried in a vacuum oven at 50° C. overnight to yield 84 mg (96%) of the title compound as a light yellow solid. HPLC/MS (method B): retention time=3.11 min, [M+H]⁺=368.0.

Preparation 1E: (S)-Methyl 4-(2-(4-(4-(6-chlorobenzo[d]thiazol-2-ylamino)phenyl)pyridin-2-yl)hydrazinyl)-2-isopropyl-4-oxobutanoate

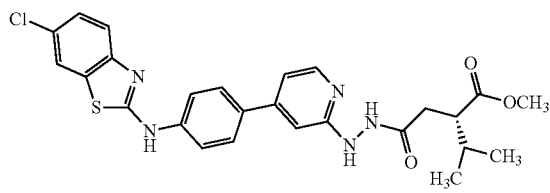

(1E)

To a solution of Compound 1D (40 mg, 0.109 mmol) in anhydrous DMF (0.5 mL) was added (S)-3-(methoxycarbonyl)-4-methylpentanoic acid (28.3 mg, 0.131 mmol), EDC (27.2 mg, 0.142 mmol), and HOBt (29 mg, 0.218 mmol), followed by a drop of DIPEA. The reaction mixture was stirred at room temperature for 16 h. Analysis by LC/MS indicated the reaction was complete. The reaction mixture was partitioned between EtOAc and water, then the separated EtOAc layer washed with water, saturated aqueous NaHCO₃, saturated aqueous NaCl (2×), dried (anhydrous Na₂SO₄), and concentrated. The obtained residue was dried in high vacuum for 1.5 h to afford 55 mg (96%) of the title compound. HPLC/MS (method A): retention time=1.88 min, [M+H]⁺=524.4.

Preparation 1F: (S)-Methyl 2-((7-(4-(6-chlorobenzo[d]thiazol-2-ylamino)phenyl)-[1,2,4]triazolo[4,3-a]pyridin-3-yl)methyl)-3-methylbutanoate

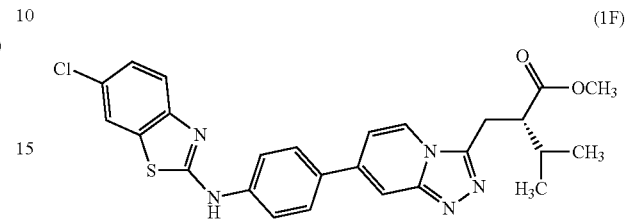

(1F)

To a turbid solution of Compound 1E (55 mg, 0.105 mmol) and DIPEA (0.14 mL, 0.8 mmol) in anhydrous THF (1 ml) was added dichlorotriphenylphosphorane (118 mg, 0.35 mmol) in small portions. During the addition, bubbles emerged in the reaction, then gradually dispersed. The resulting clear brownish solution was stirred at room temperature for 3 h, then quenched with water and extracted with EtOAc (2×30 mL). The combined EtOAc extracts were washed with water (2×), saturated aqueous NaCl (2×), dried (anhydrous Na₂SO₄), and concentrated to yield a reddish residue. The crude product was purified using preparative reverse phase HPLC (PHENOMENEX® Luna 5 μM C-18, 30×100 mm column eluting with a gradient of 50-90% B over 10 min, hold at 90% B for 5 min, solvent A=90% H₂O, 10% MeOH, solvent B=10% H₂O, 90% MeOH). The desired fractions were concentrated. The obtained residue was dissolved in EtOAc, washed with saturated aqueous NaHCO₃, water, saturated aqueous NaCl, dried (anhydrous Na₂SO₄), and concentrated. The product was dried in high vacuum for 1 h to afford 25 mg (47%) of the title compound as an off-white solid. HPLC/MS (method B): retention tune=3.57 min, [M+H]⁺=506.2. ¹H NMR (CD₃Cl, 400 MHz): δ 8.05 (d, J=7.0 Hz, 1H), 7.79 (s, 1H), 7.71 (d, J=8.8 Hz, 2H), 7.62 (d, J=8.8 Hz, 2H), 7.57 (d, J=2.2 Hz, 1H), 7.53 (d, J=8.8 Hz, 1H), 7.27 (dd, J=2.2, 8.8 Hz, 1H), 7.14 (dd, J=2.2, 8.8 Hz, 1H), 3.56 (s, 3H), 3.35 (m, 1H), 3.14 (m, 2H), 2.14 (m, 1H), 1.04 (dd, J=4.0, 6.6 Hz, 6H).

Example 1

To a cloudy solution of Compound 1F (23.5 mg, 0.047 mmol) in THF (1 ml) and MeOH (0.1 mL) was added 2 M aqueous LiOH solution (0.25 mL). The resulting yellow solution was stirred at room temperature for 16 h. Analysis by LC/MS indicated the reaction was complete. The reaction was acidified to pH 3-4 by addition of 1M aqueous HCl. The resulting suspension was extracted with EtOAc (2×). The combined EtOAc extracts were washed with water, saturated aqueous NaCl, dried (anhydrous Na₂SO₄), and concentrated under reduced pressure. The crude product was purified using preparative reverse phase HPLC (PHENOMENEX® Luna 5 μM C-18, 30×100 mm column eluting with a gradient of 50-90% B over 10 min, hold at 90% B for 5 min, solvent A=90% H₂O, 10% MeOH, solvent B=10% H₂O, 90% MeOH). The desired fractions were concentrated. The obtained residue in acetonitrile/water was lyophilized to afford the title compound in TFA salt form as yellow powder (22.6 mg, 80% yield). HPLC/MS (method B): retention time=3.41 min, [M+H]$^+$=492.1. $^1$H NMR (CD$_3$OD, 400 MHz): δ 8.85 (d, J=7.5 Hz, 1H), 8.14 (s, 1H), 7.95 (m, 5H), 7.75 (d, J=2.2 Hz, 1H), 7.59 (d, J=8.8 Hz, 1H), 7.34 (dd, J=2.2, 8.8 Hz, 1H), 3.35 (dd, J=5.2, 11.0 Hz, 1H), 3.28 (m, 1H), 3.14 (m, 1H), 2.28 (m, 1H), 1.14 (d, J=6.6 Hz, 6H). Enantiomeric excess determination (Method D, isocratic with 30% solvent A and 70% solvent B) indicated 73% e.e. (major peak: retention time at 10.71 min, minor peak: retention time at 13.53 min).

Alternatively, (S)-2-((7-(4-(6-chlorobenzo[d]thiazol-2-ylamino)phenyl)-[1,2,4]triazolo[4,3-a]pyridin-3-yl)methyl)-3-methylbutanoic acid (1G) can be prepared by the procedures described below:

Preparation 1H: Preparation of 4-bromo-2-hydrazinylpyridine

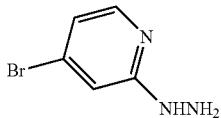

To a solution of 2-fluoro-4-bromopyridine (3.0 g, 17.15 mmol) in pyridine (30 mL) was added anhydrous hydrazine (11 mL, 0.17 mol). The resulting mixture was stirred at 75° C. for 4 h. After cooling to room temperature, the reaction mixture was concentrated to dryness under reduced pressure. To the residue was added water (60 mL), the resulting suspension was stirred at room temperature for 1 h, and then filtered. The collected solid was rinsed with water (2×), then dried in vacuum oven at 50° C. overnight to yield 2.912 g (91%) of the title compound as a light brown solid. The HPLC/MS (method B): retention time=0.60 min, [M+H]$^+$=187.9, 189.9.

Preparation 1I: (S)-Methyl 4-(2-(4-bromopyridin-2-yl)hydrazinyl)-2-isopropyl-4-oxobutanoate

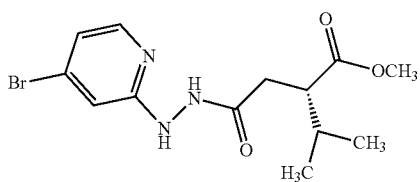

To a solution of (S)-3-(methoxycarbonyl)-4-methylpentanoic acid (216 mg, 1.24 mmol) in anhydrous DMF (3 mL) were added EDC (240 mg, 1.25 mmol) and HOBt (182 mg, 1.35 mmol). The resulting mixture was stirred at room temperature for 20 min, then Compound 1H (187 mg, 1.0 mmol) was added, followed by dropwise addition of DIPEA (0.175 mL, 1.0 mmol). The resulting mixture was stirred at room temperature for 3.5 h. Analysis by LC/MS indicated the reaction was complete. The reaction mixture was partitioned between EtOAc and water, the separated EtOAc layer washed with water, saturated aqueous NaHCO$_3$ (2×), saturated aqueous NaCl, dried (anhydrous Na$_2$SO$_4$), and concentrated. The crude product was purified using a silica gel cartridge (40 g) eluting with a gradient of EtOAc (0-100%) in hexanes to give 200 mg (58.3%) of the title compound as an off-white solid. HPLC/MS (method B): retention time=1.99 min, [M+H]$^+$=344.2, 346.2.

Preparation 1J: (S)-Methyl 2-((7-bromo-[1,2,4]triazolo[4,3-a]pyridin-3-yl)methyl)-3-methylbutanoate

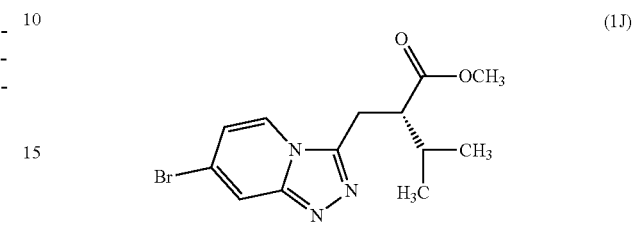

To a solution of Compound 1I (200 mg, 0.58 mmol) in anhydrous THF (3 mL) and carbon tetrachloride (2 mL) cooled at 0° C. was added DIPEA (1.01 mL, 5.8 mmol), followed by dropwise addition of triethylphosphine (0.43 mL, 2.91 mmol). The resulting cloudy solution was stirred at <5° C. for 2 h. Analysis by LC/MS indicated the reaction was not complete. To the reaction mixture was added CH$_2$Cl$_2$ (4 mL), followed by additional amount of DIPEA (0.5 mL, 2.9 mmol) and triethylphosphine (0.21 mL, 1.45 mmol). The reaction was allowed to stir at 0° C. for 2 hours, then at room temperature for 4 more hours. Analysis by LC/MS indicated the reaction was complete. The reaction was quenched by addition of water, then extracted with EtOAc (2×). The EtOAc extracts were washed with 0.5 N aqueous HCl, water (2×), saturated aqueous NaCl, dried (anhydrous Na$_2$SO$_4$), and concentrated. The crude product was purified using a silica gel cartridge (12 g) eluting with a gradient of EtOAc (0-80%) in hexanes to afford 58 mg (31%) of the title compound as a colorless glassy residue. HPLC/MS (method B): retention time=2.16 min, [M+H]$^+$=326.2, 328.2.

Example 1

To a suspension of Compound 1B (86 mg, 0.223 mmol), Compound 1J (58 mg, 0.178 mmol), potassium carbonate (61 mg, 0.446 mmol) in dioxane (2.0 mL) and water (0.7 mL) were added Pd(Ph$_3$P)$_4$ (21 mg, 0.018 mmol). The resulting yellow suspension was vigorously stirred at 100° C. for 2 h. Analysis by LC/MS indicated the reaction was complete. After cooling to room temperature, the reaction was partitioned between EtOAc and water. The water layer was extracted with EtOAc (2×), and the combined EtOAc washed with water, saturated aqueous NaCl, dried (anhydrous Na$_2$SO$_4$), and concentrated. The crude product was dissolved in a mixed solvent of THF (3 mL) and MeOH (1 mL), treated with 2 M aqueous LiOH (0.9 mL). The resulting yellow solution was stirred at room temperature for 12 h. Analysis by LC/MS indicated the reaction was complete. The reaction was acidified to pH 3-4 by addition of 1N aqueous HCl. The resulting suspension was extracted with EtOAc (2×). The combined EtOAc extracts were washed with water, saturated aqueous NaCl, dried (anhydrous Na$_2$SO$_4$), and concentrated under reduced pressure. The crude product was purified using preparative reverse phase HPLC (PHENOMENEX® Luna 5 µM C-18, 30×100 mm column eluting with a gradient of 50-90% B over 10 min, hold at 90% B for 5 min, solvent A=90% H$_2$O, 10% MeOH, solvent B=10% H$_2$O, 90% MeOH). The desired fractions were concentrated. The residue was taken into acetonitrile and lyophilized to afford the title compound as yellow lyophilate (59 mg, 67% over 2 steps). HPLC/MS (method C): retention time=1.95 min, [M+H]⁺=492.2. ¹H NMR (DMSO-d6, 400 MHz): δ 8.72 (d, J=7.5 Hz, 1H), 8.11 (s, 1H), 7.95 (m, 5H), 7.63 (d, J=8.8 Hz, 2H), 7.37 (dd, J=2.2, 8.8 Hz, 1H), 3.40 (dd, J=5.2, 11.0 Hz, 1H), 3.20 (dd, J=3.6, 11.0 Hz, 1H), 2.95 (m, 1H), 2.11 (m, 1H), 1.14 (t, J=7.2 Hz, 6H). Enantiomeric excess determination (Method D) indicated 84% e.e. (major peak: retention time at 15.97 min, minor peak: retention time at 21.71 min). The major peak was isolated using a chiral preparative column (Wheck-01 (R,R), 250×21.1 mm ID, 5 μM) at 27° C., eluting with a critic mobile phase of 25% EtOH-75% heptane-0.1% TFA at flow rate 20 mL/min, UV detection at 351 mn to afford 51.4 mg of the title compound as a yellow solid with 99.1% e.e. (determined using Method D).

Example 2

(R)-2-((7-(4-(6-Chlorobenzo[d]thiazol-2-ylamino)phenyl)-[1,2,4]triazolo[4,3-a]pyridin-3-yl)methyl)-3-methylbutanoic acid

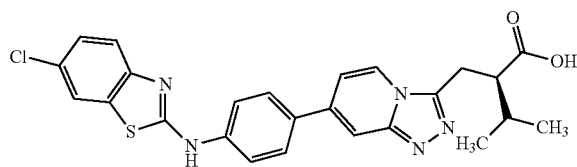

(2)

Preparation 2A: (R)-Methyl 4-(2-(4-(4-(6-chlorobenzo[d]thiazol-2-ylamino)phenyl)pyridin-2-yl)hydrazinyl)-2-isopropyl-4-oxobutanoate

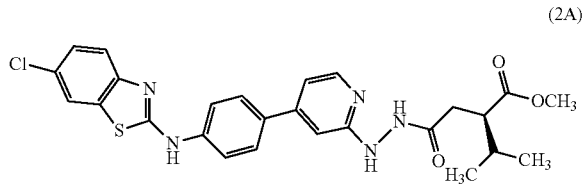 [SMILES: COC(=O)[C@H](CC(=O)NNc1cc(-c2ccc(Nc3nc4ccc(Cl)cc4s3)cc2)ccn1)C(C)C]

(2A)

To a solution of Compound 1D (40 mg, 0.108 mmol) in anhydrous DMF (0.5 mL) was added (R)-3-(methoxycarbonyl)-4-methylpentanoic acid (28.3 mg, 0.131 mmol), EDC (27.2 mg, 0.142 mmol), HOBt (29 mg, 0.218 mmol), followed by a drop of DIPEA. The reaction mixture was stirred at room temperature for 3 h. Analysis by LC/MS indicated the reaction was complete. The reaction mixture was quenched with water and then extracted with EtOAc (2×40 mL). The combined EtOAc extracts were washed with water, saturated aqueous NaHCO₃, saturated aqueous NaCl, dried (anhydrous Na₂SO₄), and concentrated. The obtained residue was dried in high vacuum to afford 52 mg (91%) of the title compound. HPLC/MS (method B): retention time=3.44 min, [M+H]⁺=524.2.

Preparation 2B: (R)-Methyl 2-((7-(4-(6-chlorobenzo[d]thiazol-2-ylamino)phenyl)-[1,2,4]triazolo[4,3-a]pyridin-3-yl)methyl)-3-methylbutanoate

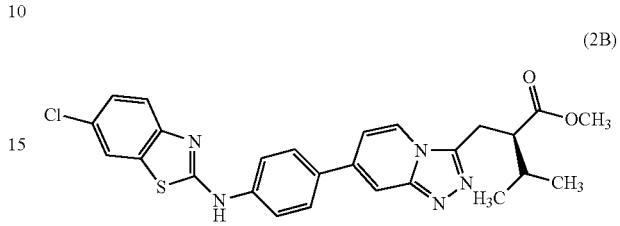

(2B)

To a solution of Compound 2A (52 mg, 0.1 mmol) in anhydrous THF (1 ml) was added DIPEA (0.14 mL, 0.8 mmol), followed by portionwise addition of dichlorotriphenylphosphorane (117 mg, 0.35 mmol). During the addition, bubbles emerged in the reaction, then gradually dispersed. The resulting clear brownish solution was stirred at room temperature for 5 h. HPLC/MS analysis indicated the reaction was complete. The reaction was quenched with water and extracted with EtOAc (2×30 mL). The combined EtOAc extracts were washed with water (2×), saturated aqueous NaCl (2×), dried (anhydrous Na₂SO₄), and concentrated to yield a reddish residue. The crude product was purified using a silica gel cartridge (12 g) eluting with a gradient of EtOAc (0-100%) in hexanes. The desired product came out of the silica gel column at 100% EtOAc flushing as a very broad peak, which resulted in collecting only part of the fractions by the auto collector. The collected fractions were concentrated under reduced pressure to afford 9.5 mg of the title compound as an off-white solid. HPLC/MS (method B): retention time=3.58 min, [M+H]⁺=506.1. ¹H NMR (CD₃Cl, 400 MHz): δ 8.10 (d, J=7.5 Hz, 1H), 7.84 (s, 1H), 7.74 (d, J=8.8 Hz, 2H), 7.68 (d, J=8.8 Hz, 2H), 7.59 (d, J=2.2 Hz, 1H), 7.54 (d, J=8.8 Hz, 1H), 7.30 (dd, J=2.2, 8.8 Hz, 1H), 7.14 (dd, J=2.2, 8.8 Hz, 1H), 3.60 (s, 3H), 3.42 (m, 1H), 3.20 (m, 2H), 2.14 (m, 1H), 1.09 (dd, J=4.0, 6.6 Hz, 6H).

Example 2

To a solution of Compound 28 (8 mg, 0.016 mmol) in THF (0.5 ml) was added 2 M aqueous LiOH solution (0.1 mL). The resulting yellow solution was stirred at room temperature for 16 h. Analysis by LC/MS indicated the reaction was complete. The reaction was acidified to pH 4 by addition of 1N aqueous HCl. The resulting suspension was extracted with EtOAc (2×). The combined EtOAc extracts were washed with water, saturated aqueous NaCl, dried (anhydrous Na₂SO₄), and concentrated under reduced pressure. The crude product was purified using preparative reverse phase HPLC (PHENOMENEX® Luna 5 μM C-18, 30×100 mm column eluting with a gradient of 50-90% B over 10 min, hold at 90% B for 5 min, solvent A=90% H₂O, 10% MeOH, solvent B=10% H₂O, 90% MeOH). The desired fractions were concentrated. The obtained residue was taken into acetonitrile and lyophilized to afford 6 mg (63%) of the title compound in a TFA salt form as a yellow powder. HPLC/MS (method B): retention time=2.82 min, [M+H]⁺=492.1. ¹H NMR (CD₃OD, 400 MHz): δ 8.85 (d, J=7.5 Hz, 1H), 8.14 (s, 1H), 7.95 (m, 5H), 7.75 (d, J=2.2 Hz, 1H), 7.59 (d, J=8.8 Hz, 1H), 7.34 (dd, J=2.2, 8.8 Hz, 1H), 3.56 (dd, J=5.2, 11.0 Hz, 1H), 3.30 (m, 1H), 3.13 (m, 1H), 2.28 (m, 1H), 1.14 (d, J=6.6 Hz, 6H). Enantiomeric excess determination (Method D, isocratic with 30% solvent A and 70% solvent B) indicated 80% e.e. (major peak: retention time at 14.33 min, minor peak: retention time at 9.72 min). The major peak was isolated using a chiral preparative column (Wheck-01 (R,R), 250×21.1 mm ID, 5 μM) at 27° C. with an isocratic mobile phase of 25% EtOH-75% heptane-0.1% TFA at flow rate 20 mL/min, UV detection at 351 nm to afford the title compound as a yellow solid with 99.2% e.e. (determined using Method D).

Example 3

(R)-2-((7-(4-(6-Chlorobenzo[d]thiazol-2-ylamino) phenyl)-[1,2,4]triazolo[4,3-a]pyridin-3-yl)methyl)-4-methylpentanoic acid

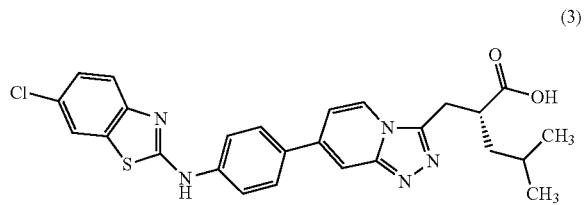 [SMILES: CC(C)C[C@H](Cc1nnc2cc(-c3ccc(Nc4nc5ccc(Cl)cc5s4)cc3)ccn12)C(=O)O]

(3)

Preparation 3A: (R)-Methyl 2-(2-(2-(4-(4-(6-chlorobenzo[d]thiazol-2-ylamino)phenyl)pyridin-2-yl) hydrazinyl)-2-oxoethyl)-4-methylpentanoate

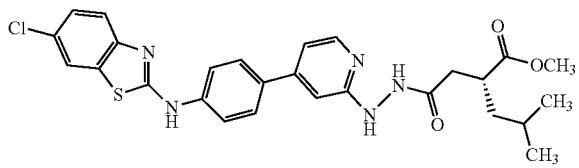

(3A)

To a solution of Compound 1D (50 mg, 0.136 mmol) in anhydrous DMF (1 mL) were added (R)-3-(methoxycarbonyl)-5-methylhexanoic acid (33 mg, 0.177 mmol), EDC (39 mg, 0.20 mmol), HOBt (27 mg, 0.20 mmol), followed by a drop of DIPEA. The reaction mixture was stirred at room temperature for 3 h. Analysis by LC/MS indicated the reaction was complete. Water was added to the reaction mixture, the white precipitate formed. The product was collected by filtration, washed with H$_2$O (3×5 mL), dried in a vacuum oven at 50° C. for 16 h to afford 70 mg (96%) of the title compound. HPLC/MS (method B): retention time=3.22 min, [M+H]$^+$= 538.3.

Preparation 3B: (R)-Methyl 2-((7-(4-(6-chlorobenzo [d]thiazol-2-ylamino)phenyl)-[1,2,4]triazolo[4,3-a] pyridin-3-yl)methyl)-4-methylpentanoate

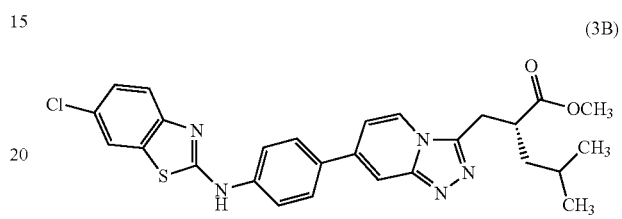

(3B)

To a solution of Compound 3A (70 mg, 0.13 mmol) in anhydrous THF (3 ml) was added DIPEA (0.19 mL, 1.1 mmol), followed by portionwise addition of dichlorotriphenylphosphane (154 mg, 0.46 mmol). The reaction was stirred at room temperature for 2 h and became a brownish clear solution. HPLC/MS analysis indicated the reaction was complete after stirring at room temperature for total 3 h. The reaction was quenched with water and extracted with EtOAc (2×30 mL). The combined EtOAc extracts were washed with water, saturated aqueous NaCl, dried (anhydrous Na$_2$SO$_4$), and concentrated to yield a reddish residue. The crude product was purified using a silica gel cartridge (12 g) eluting with a gradient of EtOAc (30-100%) in hexanes to afford 51 mg of the title compound as an off-white solid. HPLC/MS (method B): retention time=3.53 min, [M+H]$^+$=520.4. $^1$H NMR (DMSO-d$_6$, 400 MHz): δ 8.50 (d, J=7.2 Hz, 1H), 7.98 (dd, J$_1$=9.2 Hz, J$_2$=2.2 Hz, 2H), 7.86-7.95 (m, 4H), 7.63 (d, J=8.24 Hz, 2H), 7.32-7.41 (m, 2H), 3.53 (S, 3H), 3.20-3.40 (m, 2H), 3.05-3.17 (m, 1H), 1.54-1.70 (m, 2H), 1.42-1.53 (m, 1 H), 0.88 (t, J=6.3 Hz, 6H).

Example 3

To a cloudy solution of Compound 3B (50 mg, 0.096 mmol) in THF (0.5 ml) and MeOH (0.1 mL) was added 2 M aqueous LiOH solution (0.5 mL). The resulting yellow solution was stirred at room temperature for 16 h. Analysis by LC/MS indicated the reaction was complete. The reaction mixture was acidified to pH 3-4 by addition of 1N aqueous HCl. The resulting suspension was filtered. The collected solid was rinsed with water (3×5 mL) and lyophilized in acetonitrile/water to afford the title compound as a yellow lyophilate (35 mg, 72% yield). HPLC/MS (method B): retention time=3.19 min, [M+H]$^+$=506.3. $^1$H NMR (DMSO-d$_6$, 400 MHz): δ 10.80 (s, 1H), 8.65 (d, J=7.1 Hz, 1H), 8.05 (S, 1H), 7.86-7.97 (m, 5H), 7.53-7.63 (m, 2H), 7.30 (dd, J$_1$=7.1 Hz, J$_2$=2.1 Hz 1H), 3.29-3.41 (m, 1H), 3.16-3.23 (m, 1H), 2.91-3.02 (m, 1H), 1.54-1.70 (m, 2H), 1.42-1.53 (m, 1H), 0.84 (t, J=6.8 Hz, 6H). Chiral HPLC (Method D): retention time=16.89 min (e.e.=96.4%).

Example 4

(S)-2-((7-(4-(6-Chlorobenzo[d]thiazol-2-ylamino)phenyl)-[1,2,4]triazolo[4,3-a]pyridin-3-yl)methyl)-4-methylpentanoic acid

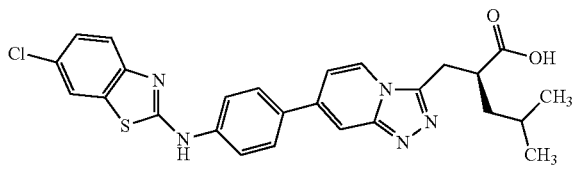

(4)

Preparation 4A: (S)-Methyl 2-(2-(2-(4-(4-(6-chlorobenzo[d]thiazol-2-ylamino)phenyl)pyridin-2-yl)hydrazinyl)-2-oxoethyl)-4-methylpentanoate

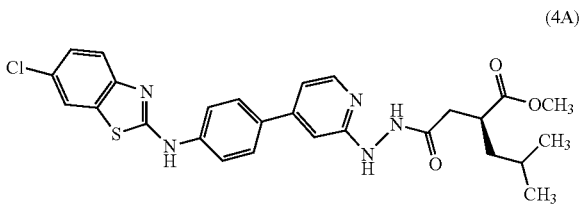 [SMILES: COC(=O)[C@H](CC(=O)NNc1cc(-c2ccc(Nc3nc4ccc(Cl)cc4s3)cc2)ccn1)CC(C)C]

(4A)

The title compound was prepared from Compound 1D and (S)-3-(methoxycarbonyl)-5-methylhexanoic acid by analogous procedures described in Example 3A. HPLC/MS (method B): retention time=3.09 min, [M+H]$^+$=538.3.

Preparation 4B: (S)-Methyl 2-((7-(4-(6-chlorobenzo[d]thiazol-2-ylamino)phenyl)-[1,2,4]triazolo[4,3-a]pyridin-3-yl)methyl)-4-methylpentanoate

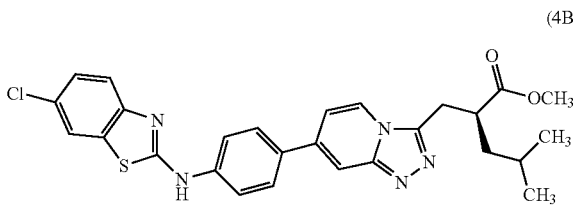

(4B)

The title compound was prepared from Compound 4B by analogous procedures described in Example 3C. HPLC/MS (method B): retention time=3.49 min, [M+H]$^+$=506.3. $^1$H NMR (DMSO-d$_6$, 400 MHz): δ 10.94 (s, 1H), 8.65 (d, J=7.1 Hz, 1H), 8.05 (S, 1H), 7.86-7.97 (m, 5H), 7.57 (d, J=8.8 Hz, 2H), 7.30 (dd, J$_1$=7.1 Hz, J$_2$=2.1 Hz, 1H), 3.29-3.41 (m, 1H), 3.16-3.23 (m, 1H), 2.91-3.02 (m, 1H), 1.54-1.70 (m, 2H), 1.42-1.53 (m, 1H), 0.84 (t, J=6.8 Hz, 6H). Chiral HPLC (Method D): retention time=23.40 min (e.e.=94.9%).

Example 5

(R)-2-((7-(4-(6-Chlorobenzo[d]thiazol-2-ylamino)phenyl)-[1,2,4]triazolo[4,3-a]pyridin-3-yl)methyl)hexanoic acid

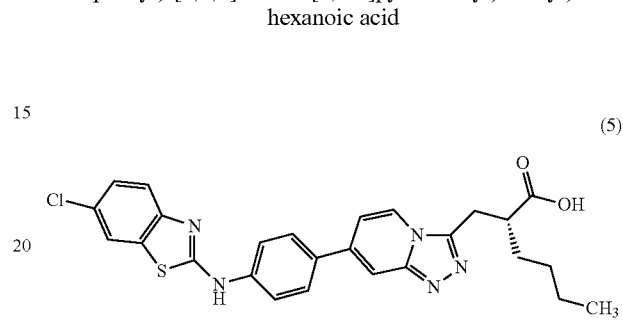

(5)

The title compound was prepared from Compound 1D and (R)-3-(methoxycarbonyl)heptanoic acid by analogous procedures described in Example 3. HPLC/MS (method B): retention time=3.54 min, [M+H]$^+$=506.3. $^1$H NMR (DMSO-d$_6$, 400 MHz): δ 10.91 (s, 1H), 8.68 (d, J=7.1 Hz, 1H), 8.06 (s, 1H), 7.86-7.97 (m, 5H), 7.52-7.62 (m, 2H), 7.30 (dd, J$_1$=7.1 Hz, J$_2$=2.1 Hz, 1H), 3.29-3.41 (m, 1H), 3.16-3.23 (m, 1H), 2.88-2.98 (m, 1H), 1.54-1.65 (m, 2H), 1.42-1.53 (m, 4H), 0.82 (t, J=6.6 Hz, 3H).). Chiral HPLC (Method D): retention time=16.89 min (e.e.=97.0%).

Example 6

(R)-3-(7-(4-(6-Chlorobenzo[d]thiazol-2-ylamino)phenyl)-[1,2,4]triazolo[4,3-a]pyridin-3-yl)-2-(cyclohexylmethyl)propanoic acid

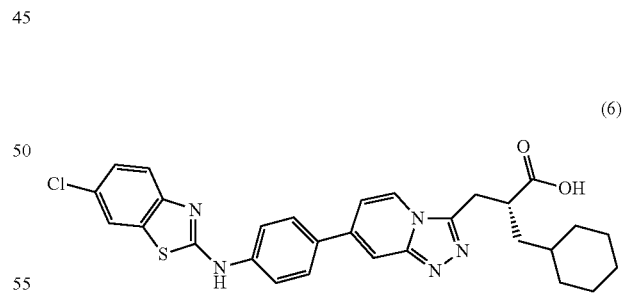

(6)

The title compound was prepared from Compound 10 and (R)-3-(cyclohexylmethyl)-4-methoxy-4-oxobutanoic acid by analogous procedures described in Example 3. HPLC/MS (method B): retention time=3.79 min, [M+H]$^+$=546.4. $^1$H NMR (DMSO-d$_6$, 400 MHz): δ 10.89 (s, 1H), 8.73 (d, J=7.1 Hz, 1H), 8.13 (s, 1H), 7.91-8.05 (m, 5H), 7.61-7.72 (m, 2H), 7.36 (dd, J$_1$=7.1 Hz, J$_2$=2.1 Hz, 1H), 3.35-3.45 (m, 1H), 3.23-3.32 (m, 1H), 3.03-3.12 (m, 1H), 1.72-1.80 (m, 1H), 1.54-1.72 (m, 5H), 1.42-1.55 (m, 1H), 1.32-1.41 (m, 1H), 1.04-1.17 (m, 3 H), 0.80-0.97 (m, 2H).). Chiral HPLC (Method D): retention time=16.89 min (e.e.=97.2%).

Example 7

(S)-3-(7-(4-(6-Chlorobenzo[d]thiazol-2-ylamino)phenyl)-[1,2,4]triazolo[4,3-a]pyridin-3-yl)-2-cyclohexylpropanoic acid

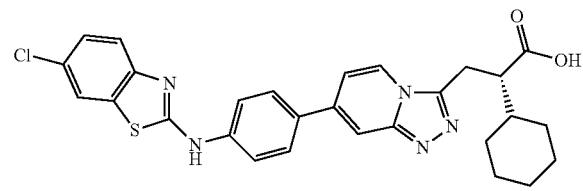

(7)

The title compound was prepared from Compound 1D and (S)-3-cyclohexyl-4-methoxy-4-oxobutanoic acid by analogous procedures described in Example 3. HPLC/MS (method B): retention time=3.68 min, [M+H]$^+$=532.3. $^1$H NMR (DMSO-d$_6$, 400 MHz): δ 10.83 (s, 1H), 8.63 (d, J=7.2 Hz, 1H), 8.08 (s, 1H), 7.91-8.05 (m, 5H), 7.63 (d, J=8 Hz, 1H), 7.51 (d, J=7.2 Hz, 1H), 7.36 (dd, J$_1$=7.1 Hz, J$_2$=2.1, Hz 1H), 3.32-3.45 (m, 1H), 3.23-3.32 (m, 1H), 2.90-2.97 (m, 2H), 1.56-1.83 (m, 4H), 1.04-1.32 (m, 6H).). Chiral HPLC (Method D): retention time=16.72 min (e.e.=90.2%).

Example 8

3-(7-(4-(6-Chlorobenzo[d]thiazol-2-ylamino)phenyl)-[1,2,4]triazolo[4,3-a]pyridin-3-yl)propanoic acid

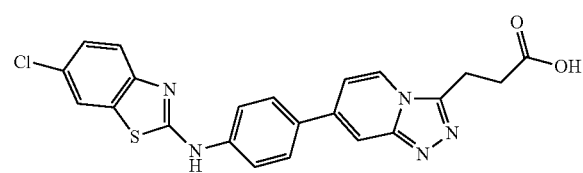

(8)

The title compound was prepared from Compound 1D and 4-methoxy-4-oxobutanoic acid by analogous procedures described in Example 3. HPLC/MS (method B): retention time=3.07 min, [M+H]$^+$=450.3. $^1$H NMR (DMSO-d$_6$, 400 MHz): δ 10.79 (s, 1H), 8.61 (d, J=7.2 Hz, 1H), 8.02 (s, 1H), 7.82-7.93 (m, 5H), 7.49-7.60 (m, 2H), 7.28 (dd, J$_1$=7.1 Hz, J$_2$=2.1, Hz 1H), 5.66 (s, 1H), 3.26 (t, J=7.2 Hz, 2H), 2.81 (t, J=6.9 Hz, 2H).

Biological Evaluation

DGAT1 Enzyme Assay

DGAT1 enzyme assays were conducted using membranes isolated from Sf9 insect cells expressing the recombinant human DGAT1 cDNA. The assays were conducted in 384-well plates with total volume of 25 μl at 25° C. In each assay, 300 ng of recombinant human DGAT1 membrane was incubated with 25 μM of 2-monooleoyl-glycerol and 25 μM of [$^3$H]-stearoyl-CoA in 100 mM potassium phosphate (pH 7.4) for 30 min with various concentrations of compounds delivered in DMSO. The assay was terminated by the addition of 30 μl of Stopping Solution [50 mM HEPES, 5 mg/ml Yittrium Oxide (YOX) Polylysine SPA beads, 3.33 mg/ml Fraction V BSA, 200 μM Mercuric chloride]. The signal was measured using LEADSEEKER$^{SM}$ for 5 minutes. To calculate the degree of inhibition, the zero level of enzyme activity (blank) was defined by the above assay using Sf9 cell membrane uninfected with baculovirus and the 100% level of DGAT1 enzyme activity was defined by human DGAT1 assay with the vehicle DMSO. The IC$_{50}$ values of inhibitors were determined by Excel-fit.

Table 1 shows the activities of compounds in the DGAT1 enzyme assay.

TABLE 1

| Example | DGAT1 Enzyme Assay IC$_{50}$ (μM) |
|---|---|
| 1 | 0.01 |
| 1F | 7.2 |
| 2 | 0.16 |
| 2B | 15 |
| 3 | 0.32 |
| 3B | 25 |
| 4 | 2.8 |
| 4B | 50 |
| 5 | 0.20 |
| 6 | 3.6 |
| 7 | 2.8 |
| 8 | 0.49 |

What is claimed is:
1. A compound according to Formula (I):

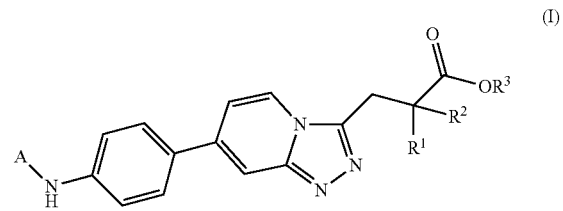

(I)

or stereoisomers or salts thereof, wherein:
A is alkyl, cycloalkyl, heterocyclyl, aryl, —C(O)R$^4$, —C(O)OR$^4$, or —C(O)NR$^4$R$^5$;
R$^1$ and R$^2$ are independently hydrogen, alkyl, —(CH$_2$)$_n$-(cycloalkyl), —(CH$_2$)$_n$-(aryl), —(CH$_2$)$_n$-(heterocyclyl), aryl, and/or heterocyclyl, or R$^1$ and R$^2$ together with the carbon atom to which they are attached, form a 3- to 7-membered cycloalkyl or 4- to 7-membered heterocyclyl ring with one or two heteroatoms;
n is an integer in the range of zero to 4;
R$^3$ is hydrogen or alkyl;
R$^4$ is alkyl, cycloalkyl, heterocyclyl, or aryl; and
R$^5$ is hydrogen or alkyl, or R$^4$ and R$^5$ together with the nitrogen atom to which they are attached, form a 4- to 7-membered heterocyclyl ring with one or two heteroatoms;
wherein:
each of said alkyl is substituted with 0-3 R$^a$;
each of said cycloalkyl is substituted with 0-3 R$^a$;
each of said heterocyclyl is substituted with 0-4 R$^b$; and
each of said aryl is substituted with 0-4 R$^b$;

$R^a$ is, independently at each occurrence, F, Cl, Br, —CF$_3$, —OH, —CN, —NR$^c$R$^d$, and/or C$_1$-C$_3$alkoxy;

$R^b$ is, independently at each occurrence, C$_1$-C$_4$alkyl, F, Cl, Br, —CF$_3$, —OH, —CN, —NR$^c$R$^d$, and/or C$_1$-C$_3$alkoxy; and $R^c$ and $R^d$ are, independently at each occurrence, H and/or C$_1$-C$_4$alkyl, or $R^c$ and $R^d$ together with the nitrogen atom to which they are attached, form a 4- to 7-membered heterocyclyl ring with one or two heteroatoms.

2. The compound according claim 1 wherein:

A is C$_1$-C$_6$alkyl, C$_3$-C$_7$cycloalkyl, 1- or 2-ring heterocyclyl, 1- or 2-ring aryl, —C(O)R$^4$, —C(O)OR$^4$, or —C(O)NR$^4$R$^5$;

R$^1$ and R$^2$ are independently hydrogen, C$_1$-C$_6$alkyl, —(CH$_2$)$_n$—(C$_3$-C$_7$cycloalkyl), aryl, and/or 1- or 2-ring heterocyclyl, or R$^1$ and R$^2$ together with the carbon atom to which they are attached, form a 3- to 7-membered cycloalkyl or 4- to 7-membered heterocyclyl ring with one or two heteroatoms;

n is an integer in the range of zero to 2;

R$^3$ is hydrogen or C$_1$-C$_6$alkyl;

R$^4$ is C$_1$-C$_6$alkyl, C$_3$-C$_7$cycloalkyl, 1- or 2-ring heterocyclyl, or aryl; and R$^5$ is hydrogen or C$_1$-C$_6$alkyl, or R$^4$ and R$^5$ together with the nitrogen atom to which they are attached, form a 4- to 7-membered heterocyclyl ring with one or two heteroatoms;

wherein:
each of said alkyl is substituted with 0-3 R$^a$;
each of said cycloalkyl is substituted with 0-3 R$^a$;
each of said heterocyclyl is substituted with 0-4 R$^b$; and
each of said aryl is substituted with 0-4 R$^b$.

3. The compound according to claim 2 wherein:

A is 1- or 2-ring heterocyclyl, or 1- or 2-ring aryl;

R$^1$ and R$^2$ are independently hydrogen, C$_1$-C$_6$alkyl, —(CH$_2$)$_n$—(C$_5$-C$_7$cycloalkyl), and/or aryl;

wherein:
each of said alkyl is substituted with 0-3 R$^a$;
each of said cycloalkyl is substituted with 0-3 R$^a$;
each of said heterocyclyl is substituted with 0-4 R$^b$; and
each of said aryl is substituted with 0-4 R$^b$.

4. The compound according to claim 3 wherein:

A is a 1- or 2-ring heterocyclyl having at least one heteroatom selected from S and N;

R$^1$ is hydrogen, C$_1$-C$_4$alkyl or —(CH$_2$)$_n$—(C$_5$-C$_7$cycloalkyl);

n is 0 or 1;

R$^2$ is hydrogen or C$_1$-C$_4$alkyl;

R$^3$ is hydrogen or C$_1$-C$_4$alkyl;

wherein:
said heterocyclyl is substituted with 0-2 R$^b$; and
R$^b$ is, independently at each occurrence, F, Cl, Br, and/or —CF$_3$.

5. The compound according to claim 4 wherein:

R$^1$ is hydrogen, propyl, butyl, cyclohexyl, or —CH$_2$-cyclohexyl;

R$^2$ is hydrogen;

R$^3$ is hydrogen or methyl; and

A is

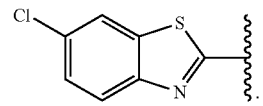

6. The compound according to claim 1 wherein said compound is:

(S)-2-((7-(4-(6-chlorobenzo[d]thiazol-2-ylamino)phenyl)-[1,2,4]triazolo[4,3-a]pyridin-3-yl)methyl)-3-methylbutanoic acid (1);

(S)-methyl 2-((7-(4-(6-chlorobenzo[d]thiazol-2-ylamino)phenyl)-[1,2,4]triazolo[4,3-a]pyridin-3-yl)methyl)-3-methylbutanoate (1F);

(R)-2-((7-(4-(6-chlorobenzo[d]thiazol-2-ylamino)phenyl)-[1,2,4]triazolo[4,3-a]pyridin-3-yl)methyl)-3-methylbutanoic acid (2);

(R)-methyl 2-((7-(4-(6-chlorobenzo[d]thiazol-2-ylamino)phenyl)-[1,2,4]triazolo[4,3-a]pyridin-3-yl)methyl)-3-methylbutanoate (2B);

(R)-2-((7-(4-(6-chlorobenzo[d]thiazol-2-ylamino)phenyl)-[1,2,4]triazolo[4,3-a]pyridin-3-yl)methyl)-4-methylpentanoic acid (3);

(R)-methyl 2-((7-(4-(6-chlorobenzo[d]thiazol-2-ylamino)phenyl)-[1,2,4]triazolo[4,3-a]pyridin-3-yl)methyl)-4-methylpentanoate (3B);

(S)-2-((7-(4-(6-chlorobenzo[d]thiazol-2-ylamino)phenyl)-[1,2,4]triazolo[4,3-a]pyridin-3-yl)methyl)-4-methylpentanoic acid (4);

(S)-methyl 2-((7-(4-(6-chlorobenzo[d]thiazol-2-ylamino)phenyl)-[1,2,4]triazolo[4,3-a]pyridin-3-yl)methyl)-4-methylpentanoate (4B);

(R)-2-((7-(4-(6-chlorobenzo[d]thiazol-2-ylamino)phenyl)-[1,2,4]triazolo[4,3-a]pyridin-3-yl)methyl)hexanoic acid (5);

(R)-3-(7-(4-(6-chlorobenzo[d]thiazol-2-ylamino)phenyl)-[1,2,4]triazolo[4,3-a]pyridin-3-yl)-2-(cyclohexylmethyl)propanoic acid (6);

(S)-3-(7-(4-(6-chlorobenzo[d]thiazol-2-ylamino)phenyl)-[1,2,4]triazolo[4,3-a]pyridin-3-yl)-2-cyclohexylpropanoic acid (7); or 3-(7-(4-(6-chlorobenzo[d]thiazol-2-ylamino)phenyl)-[1,2,4]triazolo[4,3-a]pyridin-3-yl)propanoic acid (8).

7. A pharmaceutical composition comprising a compound of claim 1 and a pharmaceutically acceptable carrier or diluent.

* * * * *